United States Patent
Takeo

(10) Patent No.: US 7,336,811 B2
(45) Date of Patent: Feb. 26, 2008

(54) METHOD AND UNIT FOR SUPPRESSING A PERIODIC PATTERN

(75) Inventor: Hideya Takeo, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 497 days.

(21) Appl. No.: 09/765,621

(22) Filed: Jan. 22, 2001

(65) Prior Publication Data

US 2001/0012407 A1 Aug. 9, 2001

(30) Foreign Application Priority Data

Jan. 20, 2000 (JP) ............................. 2000-011174

(51) Int. Cl.
  *G06K 9/00* (2006.01)
  *G06K 9/36* (2006.01)
(52) U.S. Cl. ...................... 382/132; 382/276
(58) Field of Classification Search ............... 382/128, 382/131, 132, 248, 260, 263, 264, 275, 276
  See application file for complete search history.

(56) References Cited

U.S. PATENT DOCUMENTS

| | | | |
|---|---|---|---|
| 4,258,264 A | 3/1981 | Kotera et al. ............... 250/484 |
| 4,276,473 A | 6/1981 | Kato et al. ............... 250/327.1 |
| 4,315,318 A | 2/1982 | Kato et al. ................... 364/515 |
| 5,173,788 A * | 12/1992 | Ohta ......................... 382/264 |
| 5,414,466 A | 5/1995 | Noreve et al. | |
| 6,173,086 B1 * | 1/2001 | Hara .......................... 382/276 |
| 6,269,176 B1 * | 7/2001 | Barski et al. ............... 382/128 |
| 6,333,990 B1 * | 12/2001 | Yazici et al. ................ 382/132 |

FOREIGN PATENT DOCUMENTS

| | | |
|---|---|---|
| EP | 0392504 B1 * | 9/1997 |
| EP | 0 810 769 A2 | 12/1997 |
| JP | 55-12429 | 1/1980 |
| JP | 55-116340 | 9/1980 |
| JP | 55-163472 | 12/1980 |
| JP | 56-11395 | 2/1981 |
| JP | 56-164645 | 12/1981 |
| JP | 10-164737 | 6/1998 |

OTHER PUBLICATIONS

Abstract, 56011395, Feb. 4, 1981.

(Continued)

*Primary Examiner*—Bhavesh M Mehta
*Assistant Examiner*—Charles Kim
(74) *Attorney, Agent, or Firm*—Sughrue Mion, PLLC

(57) ABSTRACT

In a wavelet transform section, wavelet-transform coefficient signals are obtained by two-dimensional wavelet transformation, employing a low-pass filter which has a characteristic that its response at a frequency greater than a spatial frequency corresponding to grid pitch is approximately zero. Based on the direction of the grid judged by a direction judging section, a suppressing section applies one-dimensional wavelet transformation to a signal containing a grid component (when a vertical grid is used, signal HL1), in the grid direction. Then, a low frequency transform coefficient signal of the transform coefficient signals is made zero. The signal, made zero, and the remaining signals, are subjected to inverse one-dimensional wavelet transformation. In an inverse wavelet transform section, the original image is restored with a signal having a suppressed grid component.

20 Claims, 13 Drawing Sheets

OTHER PUBLICATIONS

Abstract, 56164645, Dec. 17, 1981.
Abstract, 10164737, Jun. 19, 1998.
Japanese Abstract No. 2000003440, dated Jan. 7, 2000.
Bolet J-P et al: "Progress with an "all-wavelet" approach to image enhancement and de-noising of direct digital thorax radiographic images" Proceedings of 6$^{th}$ International Conference on Image Processing and its Applications, Dublin, Jul. 14-17, 1997, pp. 244-248, XP002238529.
Russ, JC: The image processing Handbook, Third edition: 1999, CRC Press, Boca Raton, FL, USA, XP002238530, p. 334-pp. 354.

* cited by examiner

F I G . 1
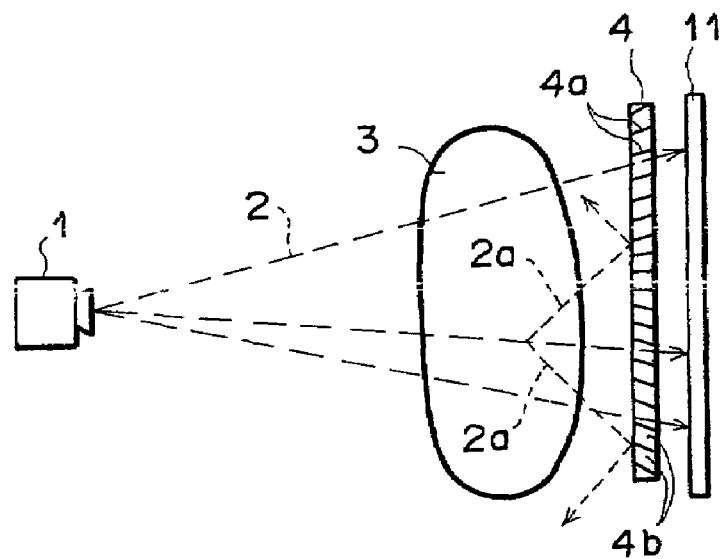
F I G . 2
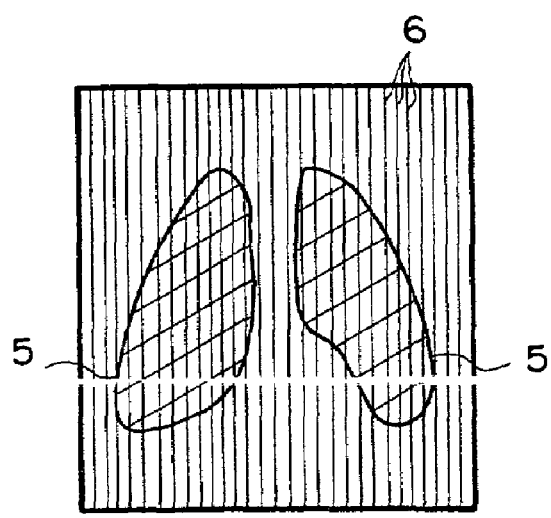

FIG. 13
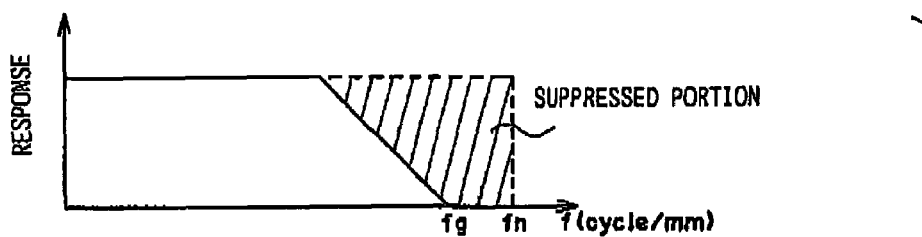
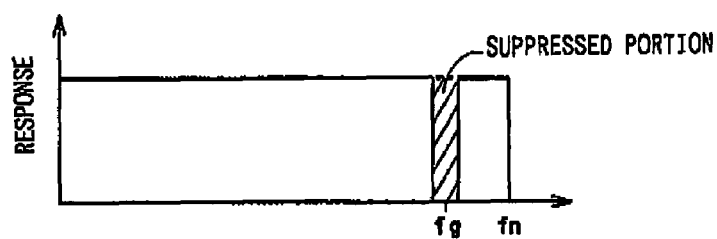
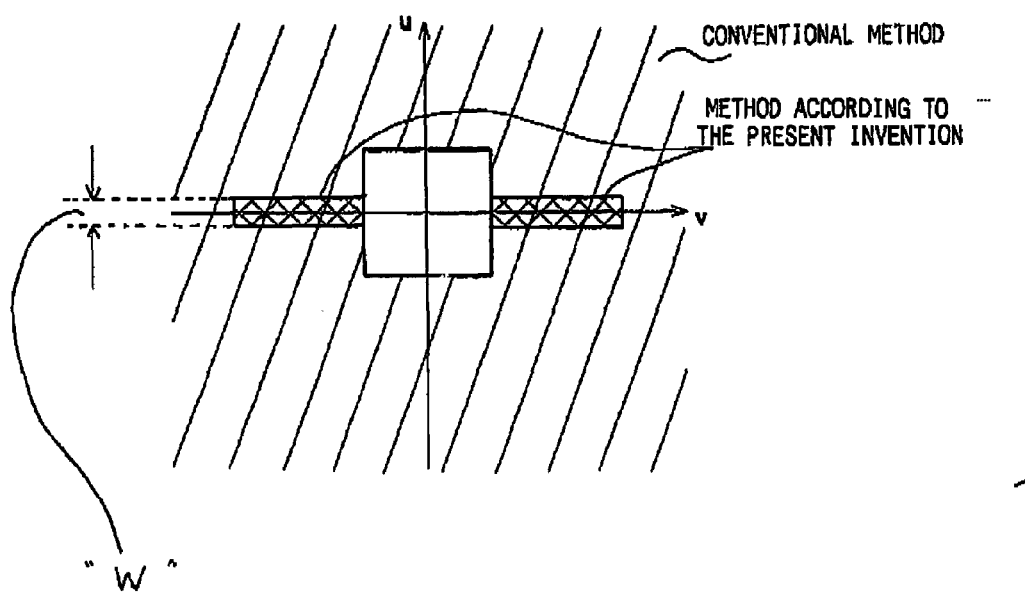

METHOD AND UNIT FOR SUPPRESSING A PERIODIC PATTERN

BACKGROUND OF THE INVENTION

1. Field of the Invention

The present invention relates to a periodic-pattern suppression method and unit, and more particularly to a method and unit for reducing and removing a stripe pattern (including a moire component), corresponding to a stationary grid, from an image photographed, for example, by use of the stationary grid, the image having the stripe pattern superposed on the image of a subject.

2. Description of the Related Art

Radiation recording-reproducing systems have been proposed in Japanese Unexamined Patent Publication Nos. 55(1980)-12429, 56(1981)-11395, 55(1980)-163472, 56(1981)-164645, 55(1980)-116340, etc. These systems utilize a storage-type phosphor (stimulatable phosphor), which stores part of radiation energy when irradiated with radiation, such as X-rays, etc., and emits photostimulated luminescent light according to the amount of the stored radiation energy when irradiated with excitation light such as visible light, etc. The radiation image of a subject, such as a human body, etc., is temporarily photographed and recorded on a storage-type fluorescent sheet. Then, excitation light, such as laser light, etc., is scanned on the storage-type fluorescent sheet to obtain photostimulated luminescent light. The obtained photostimulated luminescent light is photoelectrically read out and converted to an electrical image signal by a reading means such as a photomultiplier, etc. Based on the image signal, the radiation image of the subject is output as a visible image to a recording material such as a photosensitive material, etc., or to a cathode-ray tube (CRT) display unit, etc.

There are cases where, when photographing and recording the radiation image of a subject on the above-mentioned storage-type fluorescent sheet, photographing is performed with a stationary grid disposed between the subject and the fluorescent sheet. In the stationary grid, lead plates, which do not transmit radiation, and aluminum or wood plates, which easily transmit radiation, are alternately disposed at fine pitches of about 4 plate/mm so that radiation scattered by the subject is not irradiated to the fluorescent sheet. If photographing is performed using this stationary grid, radiation scattered by the subject will become less liable to be irradiated to the fluorescent sheet and therefore the contrast of the radiation image of the subject can be enhanced. However, the grid image in the form of a fine stripe pattern corresponding to the stationary grid, along with the subject image, is recorded.

Because of this, the applicant of this application has proposed, in Japanese Unexamined Patent Publication No. 10(1998)-164737, a method of obtaining a stripe-reduced image which is easy to observe, by applying a filtering process for removing a spatial frequency component corresponding to the stripe pattern of a stationary grid. In this method, for example, in the case where the grid array pitch (distance between the centers of adjacent grid rods) of a stationary grid (hereinafter referred to as a grid pitch) is 4 grid-line/mm, a stripe pattern develops in a spatial frequency band near 4.0 cycle/mm. In order to remove the stripe pattern, a filtering process is performed by a filter which removes or reduces its response at this frequency band.

However, the filter employed in the method in the aforementioned publication No. 10(1998)-164737 suppresses and removes not only the stripe pattern of the stationary grid but also the high frequency component contained in the original image, because its response at a frequency component near a spatial frequency corresponding to the grid pitch of a stationary grid used, and its response at a high frequency component greater than that, are made zero. Thus, there is a problem that an image will be reduced in sharpness.

SUMMARY OF THE INVENTION

The present invention has been made in view of the aforementioned circumstances. Accordingly, it is the primary object to provide a periodic-pattern suppression method and a periodic-pattern suppression unit which are capable of making a periodic pattern (such as a stripe pattern, which develops in an image because of a stationary grid, etc., and the like) inconspicuous without reducing sharpness.

To achieve this end and in accordance with a first important aspect of the present invention, there is provided a periodic-pattern suppression method of reducing a spatial frequency component which forms a periodic pattern contained in an original image signal, the method comprising the steps of:

transforming the original image signal, represented in a real space domain, into a plurality of transformed image signals which can be handled in a frequency domain; and reducing a transformed image signal of the transformed image signals which has a desired frequency range containing a spatial frequency component corresponding to at least a frequency of the periodic pattern in only the vicinity of an array direction of the periodic pattern.

The words "periodic pattern" are intended to broadly mean patterns which develop periodically in an image. For example, the periodic pattern indicates a great variety of patterns such as a stripe pattern, which occurs in an image because of a stationary grid, a moire image, which occurs in an image because of the characteristics of an imaging system in a television set, and the like.

In accordance with a second important aspect of the present invention, there is provided a periodic-pattern suppression method of reducing a spatial frequency component resulting from a stationary grid, contained in an original image signal photographed using the stationary grid, the method comprising the steps of:

transforming the original image signal, represented in a real space domain, into a plurality of transformed image signals which can be handled in a frequency domain; and reducing a transformed image signal of the transformed image signals which has a desired frequency range containing a spatial frequency component corresponding to at least a grid array frequency of the stationary grid in only the vicinity of a grid array direction of the stationary grid.

The expression "transforming into a plurality of transformed image signals" means transforming into signals to which a desired process for a desired frequency component contained in the original image signal can be applied. Particularly, in the present invention, it means transforming into signals on which a process of suppressing a frequency component, contained in the original image signal represented in a real space domain, which corresponds to the stationary grid can be applied. For example, an original image signal expressed in a real space domain can be transformed into image signals expressed in a frequency domain (frequency spectra) by Fourier transformation. Also, an original image signal expressed in a real space domain can be transformed into subband signals expressed in a frequency domain by multiresolution transformation (employing a wavelet transform or a Laplacian pyramid expansion).

The expression "spatial frequency component resulting from a stationary grid" includes not only the spatial frequency component of the stationary grid itself, but also includes a moire component which occurs due to the stationary grid by sampling at sampling cycles less than a Nyquist frequency or by a reducing process. This is why the expression "spatial frequency component corresponding to a grid array frequency" is employed. This expression means is intended to include not only the same spatial frequency component as the grid frequency but also the same spatial frequency component as the moire frequency related to this.

The expression "reducing a transformed image signal of the transformed image signals which has a desired frequency range containing a spatial frequency component corresponding to at least a grid array frequency of the stationary grid" means to apply a process for suppressing both a spatial frequency component corresponding to the grid frequency and a spatial frequency component near the grid frequency, and does not mean to suppress almost all high frequency components greater than a spatial frequency component corresponding to the grid frequency, as in the conventional method. That is, in the present invention, as fas as it is possible, high frequency components (e.g., a spatial frequency component corresponding to a Nyquist frequency and spatial frequency components near the Nyquist frequency) greater than a spatial frequency component corresponding to the grid frequency are not suppressed.

The expression "in only the vicinity of a grid array direction of the stationary grid" means to apply the suppressing process in the grid array direction of the stationary grid or the neighboring directions, and means not to apply the suppressing process in the directions other than that, unlike applying the suppressing process independently of the grid direction, as in the conventional method. The "stationary grid" used herein, as described later, may be not only a stationary grid which is actually used, but also a plurality of stationary grids, differing in grid direction, which may be used. Therefore, these stationary grids are included in the "stationary grid" in the expression "in only the vicinity of a grid array direction of the stationary grid." In other words, since the grid direction of a stationary grid that may be used in ordinary units has been determined to some degree and is, for example, a horizontal or vertical scanning direction, the process of suppressing a component corresponding to the grid frequency may be applied in the horizontal scanning direction and the vertical scanning direction orthogonal to each other. To speak in plainer language, the suppressing process maybe applied in almost all grid directions of the possible stationary grids that may be used. For instance, in a Fourier space with a horizontal scanning direction as a v-axis and a vertical scanning direction as a u-axis, only a desired spatial frequency component containing a grid frequency in the vicinity of the v-axis (having a slight width in the positive and negative directions of the u-axis orthogonal to the v-axis) and in the direction of the v-axis, and a desired spatial frequency component containing a grid frequency in the vicinity of the u-axis (having a slight width in the positive and negative directions of the v-axis orthogonal to the u-axis) and in the direction of the u-axis, may be suppressed. In this case, the grid length direction of one stationary grid is the same as the grid array direction of the other possible stationary grid, and consequently, the suppressing process is applied in both of the grid array direction and grid length direction of the possible stationary grids, which are orthogonal to each other.

In the periodic-pattern suppression method according to the present invention, it is preferable to perform the suppressing process only on a stationary grid that is actually used. Performing the suppressing process only on a stationary grid that is actually used shall mean to apply the suppressing process only in the grid array direction of a stationary grid, which is actually used, or the neighboring directions, and shall mean not to apply the suppressing process in the directions (including also the grid length direction of the stationary grid) other than that. For instance, in the case of a vertical stationary grid, it means to suppress only a component which has a desired spatial frequency range containing a grid frequency in the vicinity of the v-axis and in the direction of the v-axis.

In a preferred form of the periodic-pattern suppression method according to the present invention, the aforementioned transforming step obtains a plurality of transformed image signals by applying two-dimensional wavelet transformation to the original image signal by the use of a low-pass filter which splits a band so that its response at a frequency greater than the spatial frequency of the stationary grid becomes approximately zero. Also, the aforementioned reducing step further applies a process of reducing a component less than a predetermined frequency and then performs inverse wavelet transformation, with respect to a signal of the transformed image signals which contains a spatial frequency component corresponding to the grid array frequency.

In this case, it is more desirable that the aforementioned reducing step reduce a component less than the predetermined frequency, by recursively and repeatedly applying one-dimensional wavelet transformation to the transformed image signal (wavelet transform coefficient signal), containing a spatial frequency component corresponding to the grid array frequency, in the grid length direction of the stationary grid by a predetermined number of times by the use of a predetermined band splitting filter, then making zero transform coefficients of a low frequency image signal of a plurality of image signals obtained by one-dimensional wavelet transformation, and applying inverse one-dimensional wavelet transformation.

The "predetermined band splitting filter" does not always need to be a low-pass filter which splits a band so that its response at a frequency greater than the spatial frequency of a stationary grid becomes approximately zero.

In applying one-dimensional wavelet transformation in the grid length direction of the stationary grid, when the stationary grid is a vertical grid a HL component obtained by two-dimensional wavelet transformation is subjected to one-dimensional wavelet transformation in the vertical scanning direction, and when it is a horizontal grid an LH component obtained by two-dimensional wavelet transformation is subjected to one-dimensional wavelet transformation in the horizontal scanning direction. On the other hand, in the case of a cross grid, a HH component obtained by two-dimensional wavelet transformation is subjected to one-dimensional wavelet transformation in the horizontal scanning direction and is then subjected to one-dimensional wavelet transformation in the vertical scanning direction. Note that the order of the horizontal and vertical scanning directions may be reversed.

Besides such a method, a component less than a predetermined frequency representing the stationary grid component can also be reduced by extracting only a component representing an original image from an image signal, which contains the stationary grid component, among the image signals obtained by wavelet transformation.

In a preferred form of the periodic-pattern suppression method according to the present invention, the reducing step calculates powers of a plurality of transformed image signals, judges the grid length direction of the stationary grid, based on whether or not each of the calculated powers is greater than a predetermined threshold value, and applies the process for reducing a component less than a predetermined frequency, based on the result of judgement.

The periodic-pattern suppression method according to the present invention is not limited to a stationary grid that is actually used. For each grid which is to be used, the aforementioned reducing step may be performed by employing the transformed image signals obtained by the aforementioned two-dimensional wavelet transformation.

In the periodic-pattern suppression method according to the present invention, the aforementioned transforming step may obtain a plurality of transformed image signals by applying one-dimensional wavelet transformation to the original image signal in the grid length direction of the stationary grid by the use of a predetermined band splitting filter. Also, the aforementioned reducing step may further apply a process of reducing a component less than a predetermined frequency and then perform inverse wavelet transformation, with respect to a low frequency image signal of the transformed image signals which contains a spatial frequency component corresponding to the grid array frequency of the stationary grid.

Similarly, the above case is not limited to a stationary grid that is actually used. The aforementioned transforming step and the reducing step can be performed on each stationary grid to be used.

In accordance with a third important aspect of the present invention, there is provided a periodic-pattern suppression unit for reducing a spatial frequency component which forms a periodic pattern contained in an original image signal, the unit comprising the steps of:

image signal transformation means for transforming the original image signal, represented in a real space domain, into a plurality of transformed image signals which can be handled in a frequency domain; and periodic-pattern-component suppression means for reducing a transformed image signal of the transformed image signals which has a desired frequency range containing a spatial frequency component corresponding to at least frequency of the periodic pattern in only the vicinity of an array direction of the periodic pattern.

In accordance with a fourth important aspect of the present invention, there is provided a periodic-pattern suppression unit for reducing a spatial frequency component resulting from a stationary grid, contained in an original image signal photographed using the stationary grid, the unit comprising:

image signal transforming means for transforming the original image signal, represented in a real space domain, into a plurality of transformed image signals which can be handled in a frequency domain; and stationary-grid suppressing means for reducing a transformed image signal of the transformed image signals which has a desired frequency range containing a spatial frequency component corresponding to at least a grid array frequency of the stationary grid in only the vicinity of a grid array direction of the stationary grid.

In a preferred form of the periodic-pattern suppression unit according to the present invention, the image signal transforming means obtains the plurality of transformed image signals by applying two-dimensional wavelet transformation to the original image signal by the use of a low-pass filter which splits a band so that its response at a frequency greater than the spatial frequency of the stationary grid becomes approximately zero. Also, the stationary-grid suppressing means further applies a process for reducing a component less than a predetermined frequency and then performs inverse wavelet transformation, with respect to an image signal of the transformed image signals which contains a spatial frequency component corresponding to the grid array frequency of the stationary grid.

In this case, it is desirable that the stationary-grid suppressing means reduce a component less than the predetermined frequency, by recursively and repeatedly applying one-dimensional wavelet transformation to the transformed image signal, containing a spatial frequency component corresponding to the grid array frequency, in a grid array direction of the stationary grid by a predetermined number of times by the use of a predetermined band splitting filter, then making zero transform coefficients of a low frequency image signal of a plurality of image signals obtained by the one-dimensional wavelet transformation, and applying inverse one-dimensional wavelet transformation.

The periodic-pattern suppression unit according to the present invention may further include stationary grid-direction judging means for calculating powers of the plurality of transformed image signals and judging the grid length direction of the stationary grid, based on whether or not each of the calculated powers is greater than a predetermined threshold value. In this case, the stationary grid-direction judging means applies the process for reducing a component less than a predetermined frequency, based on the judgement made by the stationary grid-direction judging means.

The above-mentioned stationary-grid suppressing means, in addition to a stationary grid which is actually used, is capable of applying the process for reducing a component less than a predetermined frequency, to each stationary grid to be used.

In still another preferred form of the periodic-pattern suppression unit according to the present invention, the image signal transforming means obtains the plurality of transformed image signals by applying one-dimensional wavelet transformation to the original image signal in the grid length direction of the stationary grid by the use of a predetermined band splitting filter. Also, the stationary-grid suppressing means further applies a process for reducing a component less than a predetermined frequency and then performs inverse wavelet transformation, with respect to a low frequency image signal of the transformed image signals which contains a spatial frequency component corresponding to the grid array frequency of the stationary grid.

In the above case, the image signal transforming means may apply the one-dimensional wavelet transformation in the grid length direction of each stationary grid to be used, and the stationary-grid suppressing means may apply the reducing process and the inverse wavelet transformation to each stationary grid to be used.

According to the periodic-pattern suppression method and unit of the present invention, an image signal which represents an image having a periodic pattern is converted into a plurality of transformed image signals which can be handled in a frequency domain. Also, a transformed image signal of the transformed image signals, which has a desired frequency range containing a spatial frequency component corresponding to at least a frequency of the periodic pattern in only the vicinity of an array direction of the periodic pattern, is reduced. As a result, the periodic pattern in an image can be made inconspicuous.

In addition, in the case where a periodic pattern results from a stationary grid, an original image signal, photographed using a stationary grid, and represented in a real space domain, is transformed into a plurality of image signals which can be handled in a frequency domain. Also, among the plurality of image signals, the image signal, which has a desired frequency range containing the same spatial frequency component as the grid frequency of the stationary grid in approximately the grid array direction of the stationary grid, is reduced. Therefore, a stripe pattern resulting from the stationary grid will become inconspicuous. On the other hand, because all frequency components greater than the spatial frequency component resulting from the stationary grid are not suppressed, by that amount an image signal finally obtained will contain components near the spatial frequency component corresponding to a Nyquist frequency and therefore there is no possibility that sharpness will be reduced.

Unlike performing the suppressing process in all directions on Fourier space independently of grid direction, as in the conventional method, the stationary grid component is removed only in the grid array direction of the stationary grid and therefore there is no possibility that the image will be deteriorated more than necessary.

In the case where grid direction is known, there is no possibility that that the image will be deteriorated even more than necessary, if the aforementioned suppressing process is given only in the grid array direction of the stationary grid.

If the suppressing process is applied in the grid array directions of stationary grids (which differ in grid direction) to be used, the effect of the aforementioned suppressing process can be obtained without taking into consideration the grid direction of a stationary grid which is actually used. Particularly, the effect is great when two-dimensional wavelet transformation is performed.

If an image signal is given two-dimensional wavelet transformation by the use of a low-pass filter which splits a band so that its response at a frequency greater than the spatial frequency of the stationary grid becomes approximately zero, and if, among the image signals obtained by the wavelet transformation, the image signal containing a stationary grid component is further subjected to a process of reducing a component less than a predetermined frequency, an image with a reduced stationary grid component can be restored when the original image (resolution level 0) is restored by the use of the signal in which the component less than the predetermined frequency has been reduced.

Since the low-resolution signal component obtained by the wavelet transformation at the initial stage does not contain the stationary frequency component of the stationary grid, each wavelet-transform coefficient signal will not contain the spatial frequency component of the stationary grid, even if low-resolution image signals are obtained by further applying wavelet transformation over a plurality of stages. Therefore, even if an image is restored to an intermediate resolution level without being restored to resolution level 0 when it is restored, there is no possibility that a moire pattern resulting from the stationary grid will occur in a reduced-scale image (low-resolution image), because no grid component is contained in low-resolution signals of level 1 and levels thereafter. That is, even if an image is arbitrarily enlarged or reduced, no moire pattern will occur.

If, among a plurality of image signals obtained by recursively and repeatedly applying one-dimensional wavelet transformation to the image signal (wavelet-transform coefficient signal), containing the stationary grid component, in the grid direction by a predetermined number of times by the use of a predetermined band splitting filter, the transform coefficients of the low frequency image signal are made zero, in the case where image signals that can be handled in a frequency domain are obtained by wavelet transformation, a restored image can be made an image with only the stationary grid component suppressed, as the number of repeats is increased. Thus, an image with even higher sharpness can be obtained.

If powers of a plurality of image signals obtained by wavelet transformation are calculated and the grid direction is judged based on whether or not each of the calculated powers is greater than a predetermined threshold value, when the suppressing process is performed it is not necessary to previously know what kind of stationary grid is used in photographing.

Furthermore, if an image signal, photographed using a stationary grid, and represented in a real space domain, is subjected to one-dimensional transformation in the grid length direction of the stationary grid by the use of a predetermined band splitting filter, and if, among a plurality of image signals obtained by the wavelet transformation, the image signal on the low frequency side containing the stationary grid component is further subjected to the process of reducing a component less than a predetermined frequency, an image signal which has a desired frequency range containing a spatial frequency component resulting from the stationary grid can be reduced. When an image is restored by the use of the signal in which the component resulting from this stationary grid has been reduced, an image with a reduced grid component can be restored regardless of resolution level at which the image is restored.

BRIEF DESCRIPTION OF THE DRAWINGS

The present invention will be described in further detail with reference to the accompanying drawings wherein:

FIG. 1 is a top view showing a radiation image photographing apparatus;

FIG. 2 is a diagram showing the image of a subject and the image of a grid photographed by the radiation image photographing apparatus shown in FIG. 1;

FIG. 13 is a diagram showing advantages of the present invention; and

DESCRIPTION OF THE PREFERRED EMBODIMENTS

Figure 3:
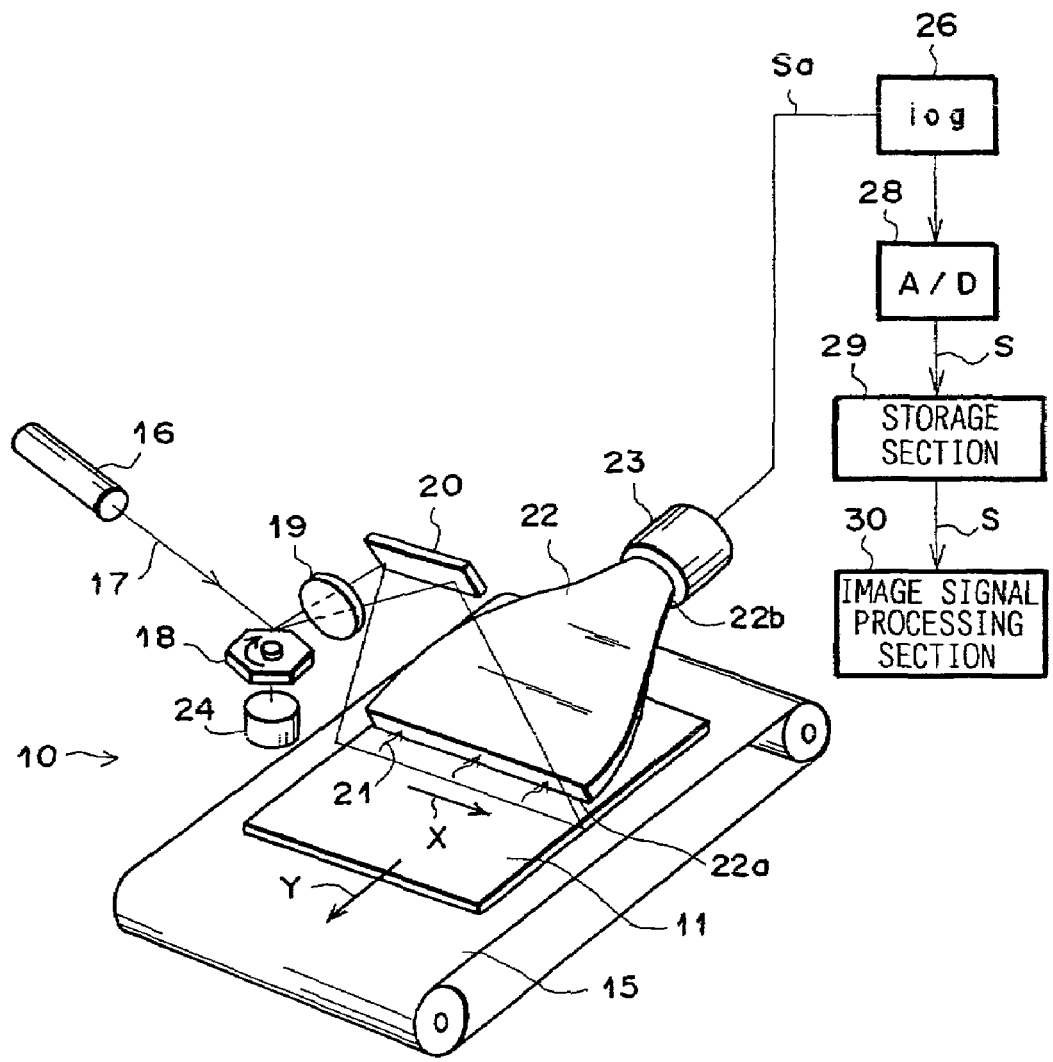
FIG. 3 is a perspective view showing a radiation image reader to which a periodic-pattern suppression unit according to the present invention, for carrying out a periodic-pattern suppression method, is applied.

A preferred embodiment of the present invention will hereinafter be described in detail with reference to the drawings. The following description will be made according to a mode, in which in a radiation image information recording-reproducing system utilizing a storage-type fluorescent sheet as a recording sheet, the radiation image of a human body recorded on the recording sheet is read out as a digital image signal by laser-beam scanning, as described in the aforementioned Japanese Unexamined Patent Publication Nos. 55(1980)-12429, 56(1981)-11395, etc.

FIG. 1 schematically shows a radiation image photographing apparatus. As shown in the figure, radiation 2 emitted from a radiation source 1 passes through a subject 3 and reaches a grid 4. In the grid 4, lead plates 4a which absorb the radiation 2 and aluminum plates 4b which transmit the radiation 2 are alternately disposed at pitches of 4 plate/mm with a slight tilt in accordance with position so that the radiation 2 emitted from the radiation source 1 is incident straight on a recording sheet 11 via the aluminum plates 4b (refer to FIG. 1). Because of this, the radiation 2, emitted from the radiation source 1, and transmitted straight through the subject 3, is absorbed and blocked by the lead plates 4, but it is transmitted through the aluminum plates 4b and irradiated to the recording sheet 11. As a result, a grid image 6 with four stripes per millimeter, along with the image of the subject 3, is stored and recorded on the recording sheet 11. On the other hand, radiation 2a scattered within the subject 3 is incident obliquely with respect to the tilt of the grid 4. Since the scattered radiation 2a incident on the aluminum plates 4b is absorbed in the lead plates 4a within the grid 4, or it is reflected at the surface of the grid 4, it is not irradiated to the recording sheet 4. Thus, a distinct radiation image with less irradiation of the scattered radiation 2a is stored and recorded on the recording sheet 11.

FIG. 2 illustrates a subject image (indicated by oblique lines) 5 and a grid image 6 in the form of a stripe pattern, stored and recorded on the recording sheet 11 by performing photographing, using the grid 4. Thus, a radiation image with the subject image 5 superposed on the grid image 6 is recorded on the recording sheet 11.

FIG. 3 illustrates a radiation image reader to which an embodiment of a periodic-pattern suppression unit according to the present invention, for carrying out a periodic-pattern suppression method, is applied.

The recording sheet 11 with the radiation image, set at a predetermined position in a reading section 10, is conveyed in a direction of arrow Y at intervals of 10 scan/mm by sheet conveying mean 10, such as an endless belt, which is driven by drive means (not shown). On the other hand, a light beam 17 emitted from a laser light source 16 is reflected and deflected by a rotating polygon mirror 18 which is driven to rotate at high speeds in an arrow-indicating direction by a motor 24. The deflected light beam 17 is passed through a focusing lens 19 such as fθ, for example. The light beam 17 is changed in direction by a mirror 20 and is incident on sheet 11 and moved in a direction approximately perpendicular to the vertical scanning direction (direction of Y arrow). From a position on the sheet 11 irradiated with the light beam 17, photostimulated luminescent light 21 with a quantity of light corresponding to the radiation image information being stored and recorded is emitted and incident on the incidence end 22a of an optical guide 22. The photostimulated luminescent light 21 is totally reflected at the internal surface of the optical guide 22 and arrives at the emergence end 22b of the optical guide 22 and is received by a photomultiplier 23. The photostimulated luminescent light 21 representing the radiation image is photoelectrically detected and converted to an electrical signal $S_a$.

The output analog signal $S_a$ is logarithmically amplified by a log amplifier 26. The amplified signal $S_a$ is sampled and digitized at sampling intervals corresponding to a spatial frequency of fs=10.0 cycle/mm by an A/D converter 28. In this manner, a digital image signal S carrying a high-density image with a high reading density is obtained. Note that the image signal S contains the information of a spatial frequency band of 4.0 cycle/mm (which is information on the grid image 6 shown in FIG. 2) lower than the highest spatial frequency (Nyquist frequency to be described later) fn=5.0 cycle/mm in a desired spatial frequency range, required to reproduce and output a satisfactory visible radiation image. Also, the information on the grid image 6 should be removed because it is one of the causes making it difficult to view the visible radiation image when observing it.

Figure 4:
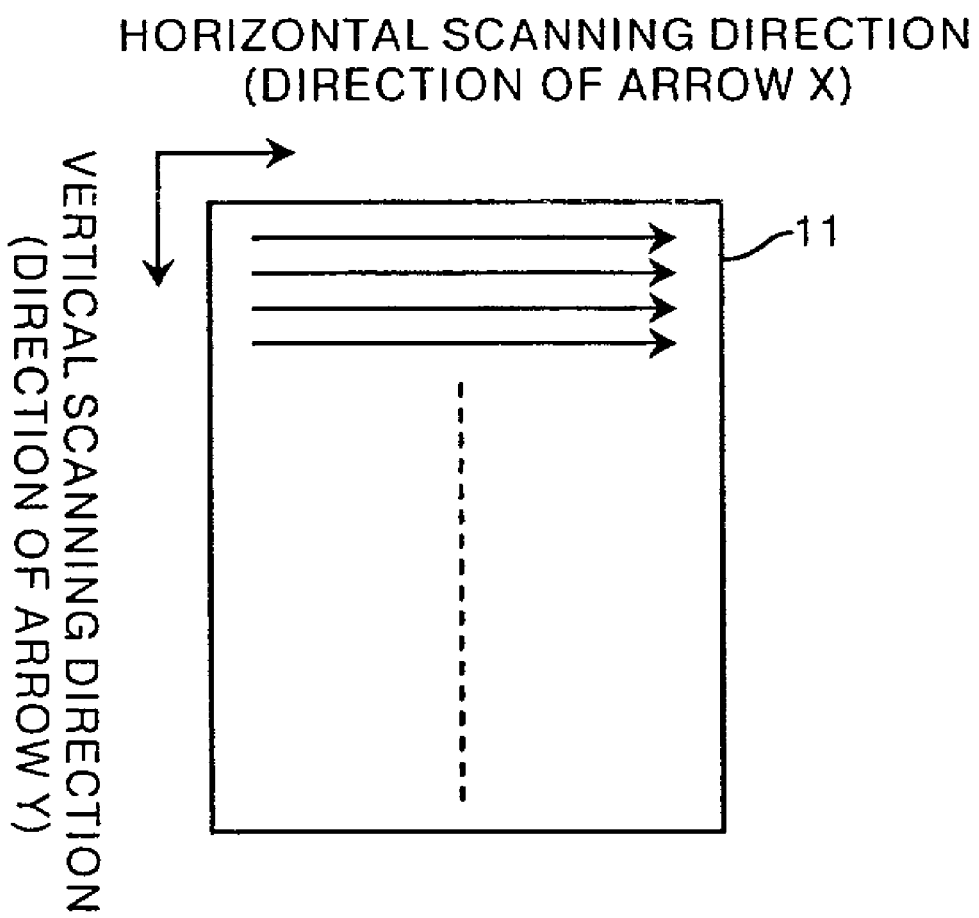
FIG. 4 is a diagram showing the relationship between scanning directions and an image to be read.

The image signal S represents image information obtained by scanning the laser beam on the sheet 11 two-dimensionally, as shown in FIG. 4. That is, the sheet 11 is moved in the vertical scanning direction (direction of arrow Y), while the laser beam is being scanned on the sheet 11 in the horizontal scanning direction (direction of arrow X). The image signal S thus obtained carries information less than Nyquist frequency fn, so it also contains the information (4.0 cycle/mm) on the grid image 6 shown in FIG. 2. In this embodiment, the moire of the grid image 6 due to aliasing will not occur because the analog signal $S_a$ is digitized at sampling intervals corresponding to the spatial frequency fs which is two or more times the frequency (4.0 cycle/mm) of the information on the grid image 6.

After being stored temporarily in a storage section 29, the image signal S is input to an image signal processing section 30 and processed in the following manner.

Figure 5:
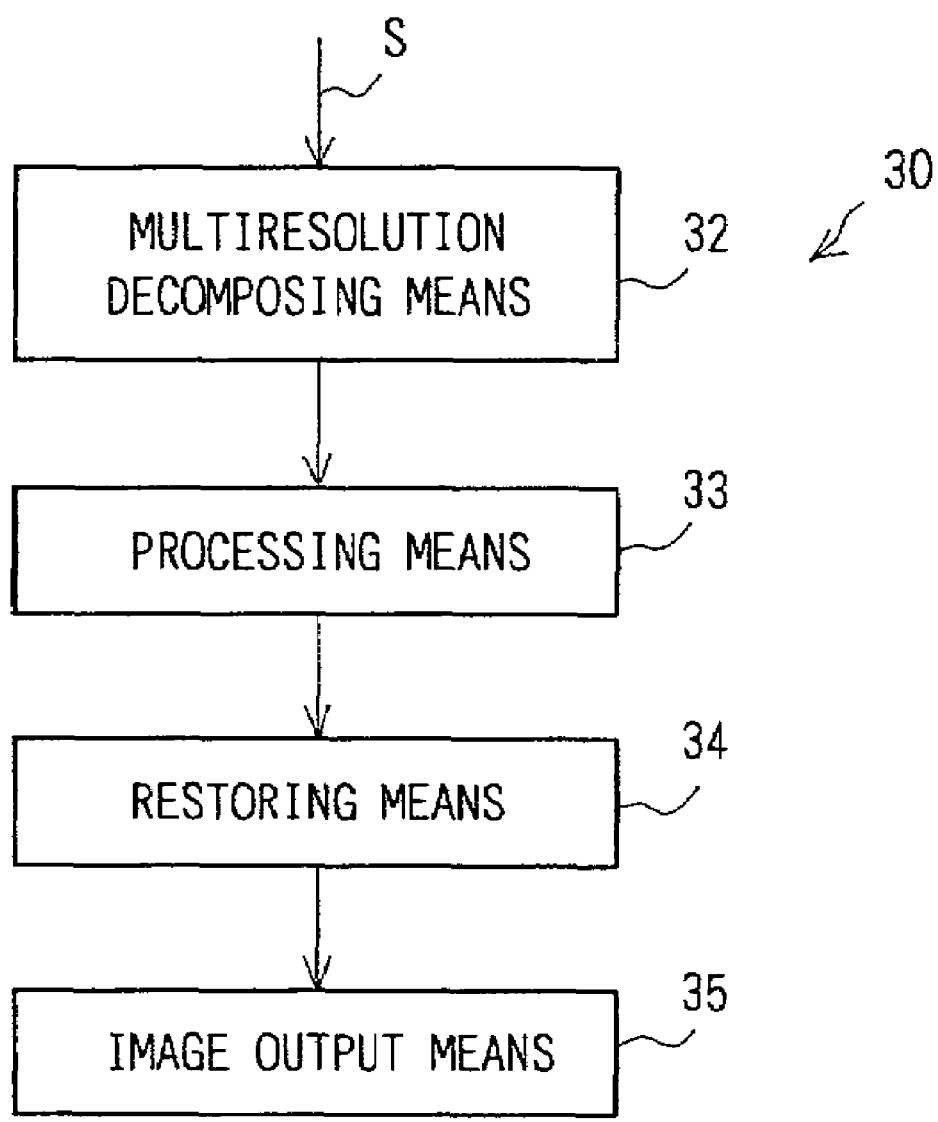
FIG. 5 is a block diagram showing an example of the image signal processing section of the periodic-pattern suppression unit of the present invention.

FIG. 5 shows the image signal processing section (one form of a periodic-pattern suppression unit) 30 for carrying out the periodic-pattern suppression method of the present invention. As shown in the figure, the image signal processing section 30 has (1) multiresolution decomposing means 32 as image signal transforming means for applying a multiresolution decomposing process to the image signal S read out from the storage section 29, (2) processing means 33 for applying a desired process (e.g., an enhancing process) to an image signal which has a predetermined frequency band (band-limited image signal), among the band-limited image signals (band-pass and sub-band signals) decomposed to a plurality of frequency bands by the multiresolution decomposing means 32, (3) restoring means 34 for obtaining a processed image signal by restoring both the band-limited image signal, subjected to the desired process by the processing means, and the band-limited image signals carrying other frequency bands, and (4) image output means 35 for reproducing a visible image, based on the processed image signal restored by the restoring means 34.

Note that in this embodiment, the multiresolution decomposing process employing a wavelet transform process is used when the image signal S represented in an actual spatial domain is transformed into image signals which can be handled in a frequency domain. Therefore, the multiresolution decomposing means 32 functions as wavelet transform means for applying wavelet transformation to the image signal S representing the radiation image, while the restoring means 34 functions inverse wavelet transform means for obtaining a processed image signal by applying an inverse wavelet transform process. In the following description, the multiresolution decomposing means 32 is referred to as a wavelet transform section 32 and the restoring means 34 is referred to as an inverse wavelet transform section 34.

Figure 6:
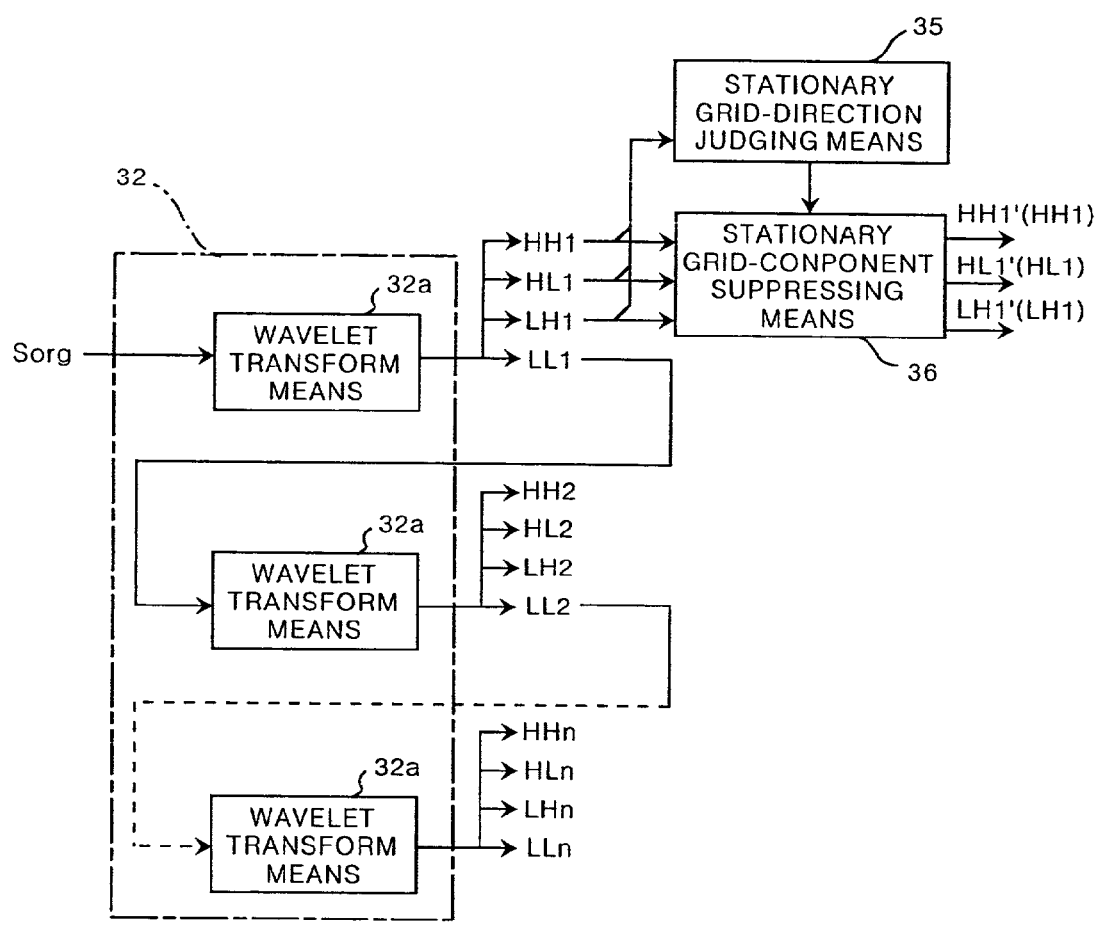
FIG. 6 is a block diagram showing how a wavelet transform process is performed by a wavelet transform section.
Figure 7:
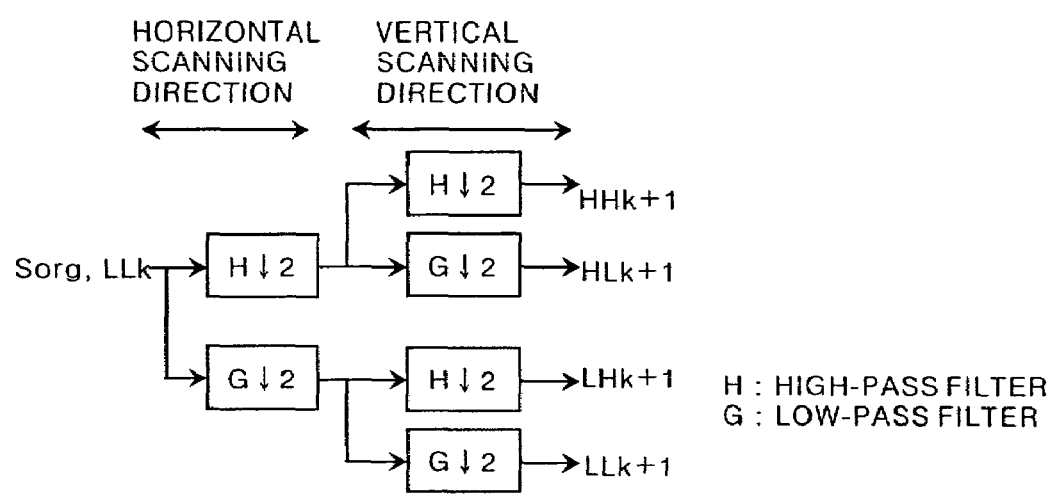
FIG. 7 is a block diagram showing wavelet transform means.

FIG. 6 shows how the wavelet transform process as the multiresolution decomposing process is performed by the wavelet transform section 32. In FIG. 7, each wavelet transform means 32a is shown in detail. As shown in FIG. 6, the wavelet transform section 32 is provided with a plurality of wavelet transform means 32a corresponding in number to resolution (pixel density) levels. Similarly, the inverse wavelet transform section 34 is provided with a plurality of inverse wavelet transform means 34a corresponding in number to the plurality of wavelet transform means 32a.

As also shown in FIG. 6, the image signal processing section 30 is equipped with stationary grid-direction judging means (hereinafter referred to as direction judging means) 35 and stationary grid-component suppressing means 36. The direction judging means 35 is used for calculating powers of signals HL1, LH1, and HH1 obtained by wavelet transformation, and for judging the grid length direction of the stationary grid 4 (i.e., grid direction), based on whether each of the calculated powers is greater than a predetermined threshold value HT1. The stationary grid-component suppressing means 36 is used to reduce an image signal of the image signals HL, LH, and HH which has a desired frequency range containing at least a spatial frequency component resulting from the stationary grid 4 in the grid array direction of the stationary grid 4 (i.e., a direction perpendicular to the grid direction).

Now, the periodic-pattern suppression method according to the present invention will be described in detail. This embodiment performs two-dimensional wavelet transformation in which wavelet transform coefficients are orthogonal to one another.

Figure 8:
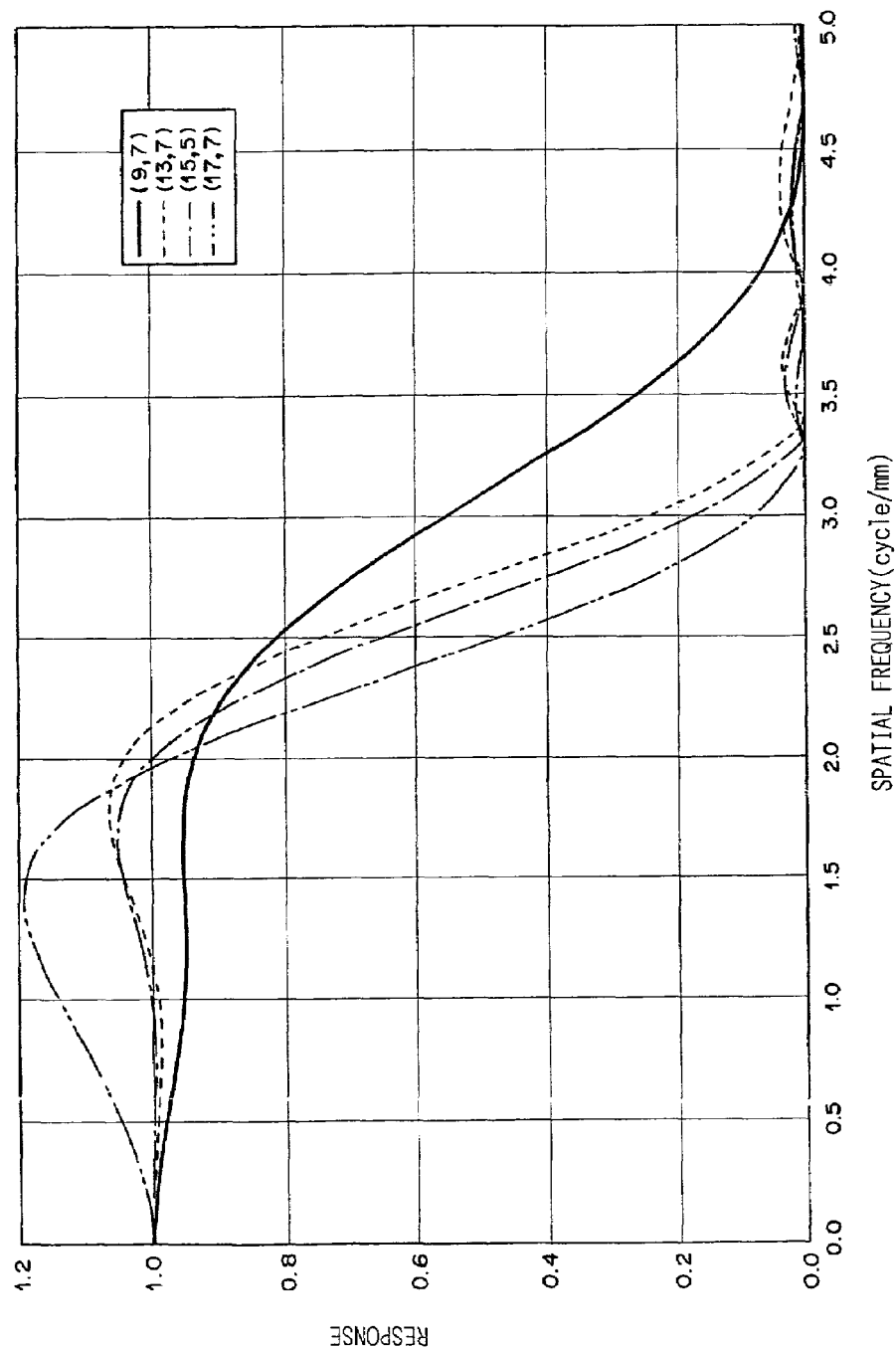
FIG. 8 is a graph showing the frequency response characteristics of the low-pass filters in wavelet transform filters.

As shown in FIGS. 6 and 7, if the digital image signal S, read out from the storage section 29, which represents the original image, is input as an original image signal $S_{ori}$ to the wavelet transform section 32, the original image signal $S_{ori}$ is subjected to wavelet transformation. More specifically, a filtering process is performed in the horizontal scanning direction of the original image signal $S_{ori}$ (equivalent to a signal LL0) by wavelet functions H1, G1, and the pixels in the horizontal scanning direction are thinned out at every other pixel, whereby the number of pixels in the horizontal scanning direction is reduced to one half. Note that the thinned-out signals obtained in this way are represented by "↑2" in FIG. 7. The function H1 is a high-pass filter, while the function G1 is a low-pass filter. Furthermore, the filtering process is performed on each of the thinned-out signals in the vertical scanning direction by the wavelet functions H1, G1, and the pixels in the vertical scanning direction are thinned out at every other pixel, whereby the number of pixels in the vertical scanning direction is reduced to one half. In this manner, wavelet-transform coefficient signals (hereinafter also referred to simply as signals) HH1, HL1, LH1, and LL1 are obtained. The signal LL1 represents a one-fourth reduction image obtained by reducing the original image to one half in both the vertical and horizontal directions. In the respective one-fourth reduction images of the original image, the signal LH1 represents an image of a high frequency component (horizontal edge) in the vertical scanning direction, the signal HL1 represents an image of a high frequency component (vertical edge) in the horizontal scanning direction, the signal HH1 represents an image of a high frequency component (diagonal edge) in the diagonal direction, and the signal LL1 represents an image of a low frequency component of half resolution with respect to the original image. The frequency which becomes a reference for band split, i.e., the frequency at the boundary between the low frequency component, and each of the high frequency components is determined by the filter characteristics of the functions H1, G1. In the filtering process by the functions H1, G1 at the initial stage, the function G1, as a low-pass filter has such a characteristic that its response at a spatial frequency of 4.0 cycle/mm or more is practically zero at the grid pitches of the stationary grid 4. Also, the function H1 as a high-pass filter has a high-pass characteristic for compensating for the low-pass characteristic of the function G1. As a filter with such a characteristic, there is, for example, a filter having the same characteristic as a moire removing filter described in Japanese Unexamined Patent Publication No. 10(1998)-164737, i.e., a filter in which its response to 97% or more of the spatial frequency component at the grid pitch of the stationary grid 4 is reduced to 5% or less. It can be realized, for example, by a wavelet transform filter employing filter coefficients, such as (17, 7)-tap coefficients listed in Table 1, (13, 7)-tap coefficients listed in Table 2, and (15, 5)-tap coefficients listed in Table 3. The frequency response characteristics of the low-pass filters in wavelet transform filters are shown in FIG. 8.

TABLE 1

(17, 7) - tap

Wavelet split low-pass filter G1
    (a8, a7, a6, a5, a4, a3, a2, a1, a0, a1, a2, a3, a4, a5, a6, a7, a8)
Wavelet split high-pass filter H1
    (b3, b2, b1, b0, b1, b2, b3)

| | |
|---|---|
| a0 = 0.53534743 | b0 = 1.26885769 |
| a1 = 0.31296897 | b1 = −0.50000000 |
| a2 = −0.02883059 | b2 = −0.13442884 |
| a3 = −0.09095774 | b3 = −0.13442884 |
| a4 = 0.01828153 | |
| a5 = 0.03402453 | |
| a6 = −0.01037186 | |
| a7 = −0.00278855 | |
| a8 = −0.00278855 | |

Wavelet synthesis low-pass filter G1'
    (−b3, b2, −b1, b0, −b1, b2, −b3)
Wavelet synthesis high-pass filter H1'
    (a8, −a7, a6, −a5, a4, −a3, a2, −a1, a0, −a1, a2, −a3, a4,
    −a5, a6, −a7, a8)

TABLE 2

(13, 7) - tap

Wavelet split low-pass filter G1
    (a6, a5, a4, a3, a2, a1, a0, a1, a2, a3, a4, a5, a6)
Wavelet split high-pass filter H1
    (b3, b2, b1, b0, b1, b2, b3)

| | |
|---|---|
| a0 = 0.5590000000 | b0 = 1.1678751323 |

TABLE 2-continued (13, 7) - tap a1 = 0.3070000000  b1 = -0.5408349230
a2 = -0.0460000000  b2 = -0.0839375665
a3 = -0.0901544756  b3 = 0.0408349233
a4 = 0.0338214681
a5 = 0.0308330075
a6 = -0.0150000000
Wavelet synthesis low-pass filter G1'
 (-b3, b2, -b1, b0, -b1, b2, -b3)
Wavelet synthesis high-pass filter H1'
 (a6, -a5, a4, -a3, a2, -a1, a0, -a1, a2, -a3, a4, -a5, a6)

TABLE 3

(15, 5) - tap

Wavelet split low-pass filter G1
 (a7, a6, a5, a4, a3, a2, a1, a0, a1, a2, a3, a4, a5, a6, a7)
Wavelet split high-pass filter H1
 (b2, b1, b0, b1, b2)
  a0 = 0.53534743    b0 = 1.26885769
  a1 = 0.31296897    b1 = -0.50000000
  a2 = -0.02883059   b2 = -0.13442884
  a3 = -0.09095774
  a4 = 0.01828153
  a5 = 0.03402453
  a6 = -0.01037186
  a7 = -0.00278855
Wavelet synthesis low-pass filter G1'
 (b2, -b1, b0, -b1, b2)
Wavelet synthesis high-pass filter H1'
 (-a7, a6, -a5, a4, -a3, a2, -a1, a0, -a1, a2, -a3, a4, -a5, a6, -a7)

With the wavelet transform filters, when a horizontal grid is used as the stationary grid 4, the grid component develops in the signal LH1. When a vertical grid is used, the grid component develops in the signal HL1. When a cross grid is used, the grid component develops in the signal HH1. In the signal LL1, a moire pattern resulting from the stationary grid 4 hardly develops regardless of grid direction, because the spatial frequency component of the stationary grid 4 has sufficiently been suppressed.

Among the wavelet-transform coefficient signals HH1, HL1, LH1, and LL1, the signals HH1, HL1, and LH1 having a possibility of containing the grid component are input to the direction judging means 35 and the grid component suppressing means 36.

Furthermore, in the wavelet transform means 32a of the second stage, the signal LL1 is subjected to wavelet transformation by the use of basic wavelet functions H0, G0, whereby signals HH2, HL2, LH2, and LL2 are obtained. The signal LL2 represents a one-sixteenth reduction image obtained by reducing the original image to one-fourth in both the vertical and horizontal directions. In the one-sixteenth reduction images of the original image, the signals HL2, LH2, and HH2 represent the images of the vertical edge, horizontal edge, and diagonal edge components, respectively. Since the grid component hardly develops in the signal LL1, as described above, the wavelet functions H0 and G0 which are employed at the second stage do not need to be set at the grid pitches of the stationary grid 4, unlike the wavelet functions H1 and G1 employed at the initial stage. For example, the wavelet functions H0, G0 may be a wavelet transform filter employing Daubechie's (9, 7)-tap filter coefficients listed in Table 4. The frequency response characteristic of the low-pass filter in this (9, 7)-tap wavelet transform filter is shown in FIG. 8.

TABLE 4

Daubechie's (9, 7) - tap

Wavelet split low-pass filter G0
 (a4, a3, a2, a1, a0, a1, a2, a3, a4)
Wavelet split high-pass filter H0
 (b3, b2, b1, b0, b1, b2, b3)
  a0 = 0.602949180    b0 = 1.115087052000
  a1 = 0.266864120    b1 = -0.591271763000
  a2 = -0.078223267   b2 = -0.057543526000
  a3 = -0.016864118   b3 = -0.091271763114
  a4 = 0.026748757
Wavelet synthesis low-pass filter G0'
 (-b3, b2, -b1, b0, -b1, b2, -b3)
Wavelet synthesis high-pass filter H0'
 (a4, -a3, a2, -a1, a0, -a1, a2, -a3, a4)

In the same manner as the aforementioned second stage, a wavelet-transform coefficient signal LLk obtained for each frequency band is subjected to wavelet transformation by n times, whereby wavelet-transform coefficient signals HH1 to HHn, HL1 to HLn, LH1 to LHn, and LL1 to LLn are obtained. The wavelet-transform coefficient signals HHn, HLn, LHn, and LLn, obtained by the nth wavelet transformation, each represent a $1/(1/2)^{2n}$ reduction image in which the number of pixels in each of the horizontal and vertical directions is $(1/2)^n$, compared with the original image signal $S_{org}$. The greater the "n" in the wavelet-transform coefficient signals HHn, HLn, LHn, and LLn, the lower the frequency band. Thus, each of the wavelet-transform coefficient signals HHk, HLk, LHk, and LLk (where k is an integer of 1 to n, representing resolution level) becomes a band-limited image signal carrying a frequency component which has a predetermined frequency range contained in the frequency range of the original image signal $S_{org}$. The signal HHk represents changes in frequency in the horizontal and vertical directions of the original image signal $S_{org}$, and becomes a lower frequency signal if k is greater. The signal HLk represents a change in frequency in the horizontal direction of the original image signal $S_{org}$, and becomes a lower frequency signal if k is greater. The signal LHk represents a change in frequency in the vertical direction of the original image signal $S_{org}$, and becomes a lower frequency signal if k is greater.

Next, in the direction judging means 35, the power of each of the signals LH1, HL1, and HH1 is calculated. Then, it is judged whether or not each power is greater than a predetermined threshold TH0. Based on the result, the grid direction of the stationary grid 4 is judged. More specifically, as described above, the grid component develops in the signal LH1 when a horizontal grid is used, develops in the signal HL1 when a vertical grid is used, and develops in the signal HH1 when a cross grid is used. Therefore, when only the power of the signal LH is greater than the threshold value TH0 it is judged that a horizontal grid has been used, when only the power of the signal HL is greater than the threshold value TH0 it is judged that a vertical grid has been used, and when both the power of the signal HL and the power of the signal LH are greater than the threshold value TH0 it is judged that a cross grid has been used. This result of judgement is input to the stationary grid-component suppressing means 36.

Next, based on the grid direction judged by the direction judging means 35, in the stationary grid-component suppressing means 36 a signal of the signals LH1, HL1, and HH1 which contains a stationary grid component is further subjected to one-dimensional wavelet transformation recursively and repeatedly by a predetermined number of times in the grid length direction of the stationary grid 4 (grid direction) by the use of a predetermined band splitting filter. For instance, in the case where a vertical grid is used as shown in FIG. 2, the signal HL1 is subjected to one-dimensional wavelet transformation in the vertical scanning direction, whereby a signal HL1 (L1), carrying a low frequency side, and a signal HL1 (H1), carrying a high frequency side, are obtained. Then, the signal HL1 (L1) carrying a low frequency side is subjected to one-dimensional wavelet transformation in the vertical scanning direction, whereby a signal HL1 (L1), carrying a low frequency side, and a signal HL1 (H1), carrying a high frequency side, are obtained. Similarly, by repeatedly performing one-dimensional wavelet transformation on the signal HL1 (Lj), which carries a low frequency side (where j is an integer of 1 to m), in the vertical scanning direction by m times, the signal HL1 is subjected to one-dimensional wavelet transformation in the vertical scanning direction over a plurality of stages (m stages), whereby wavelet-transform coefficient signals HL1 (H1) to HL1 (Hm), HL1 (Lm) are obtained.

Figures 9A, 9B:
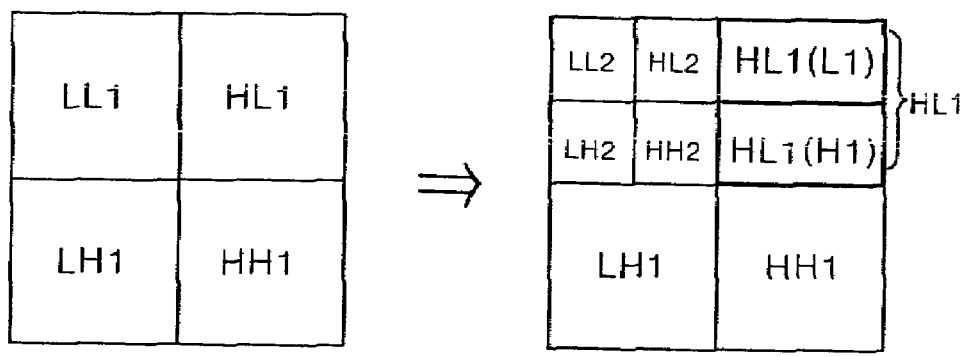
FIG. 9A is a diagram showing the decomposed components of the original image signal obtained after the original image signal has been subjected to the first two-dimensional wavelet transformation.
FIG. 9B is a diagram showing the state in which the original image signal has further been decomposed from the state of FIG. 9A.

FIG. 9 shows the decomposed components of the original image signal obtained after the original image signal has been subjected to wavelet transformation. In FIG. 9A, the first two-dimensional wavelet transformation is performed, and in FIG. 9B, after the second two-dimensional wavelet transformation the signal HL1 is subjected to one-dimensional wavelet transformation in the vertical direction once.

Figure 10:
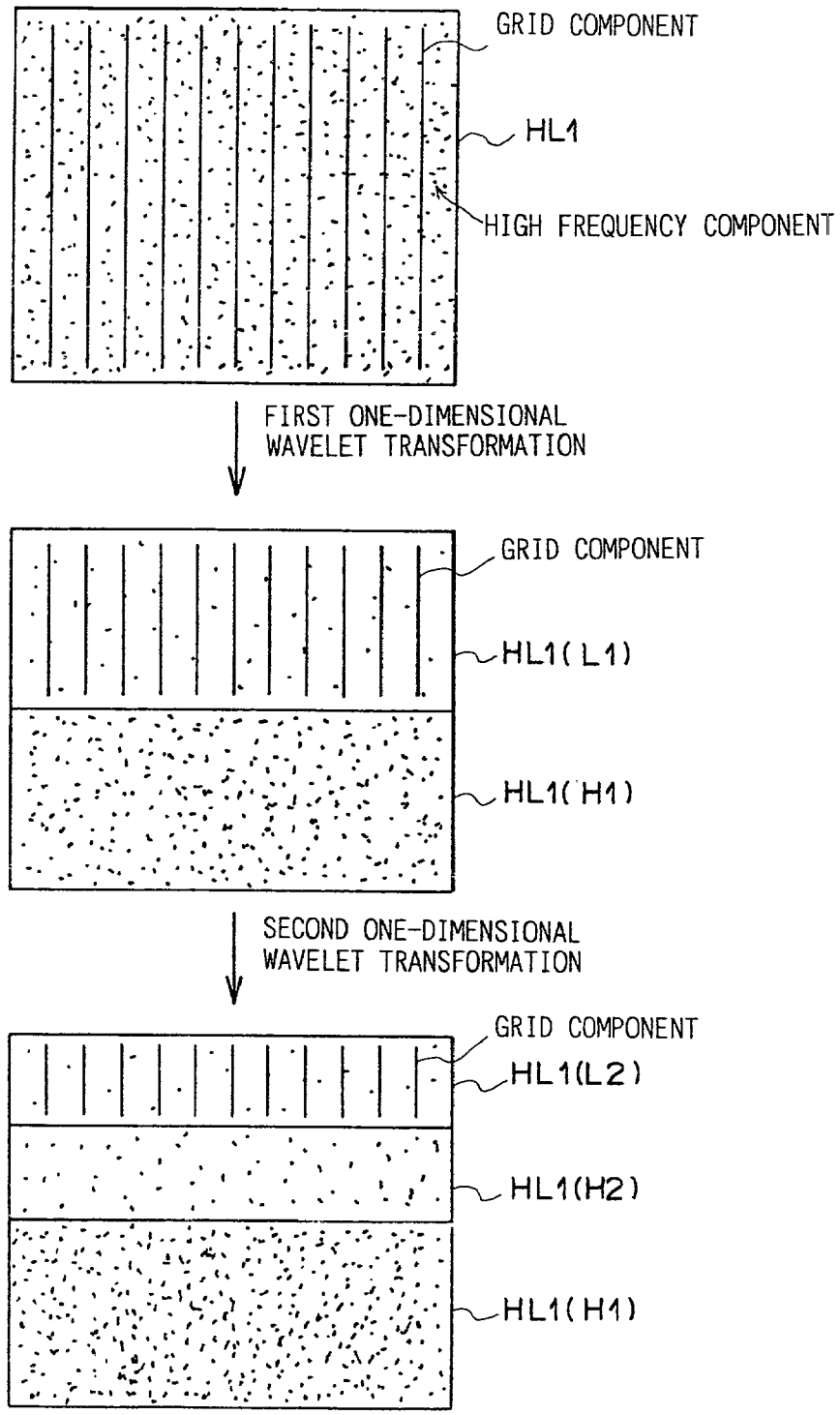
FIG. 10 is a schematic diagram showing how the effect of one-dimensional wavelet transformation is obtained by repeating the transformation.

The effects obtained by repeating one-dimensional wavelet transformation in the grid length direction are illustrated in FIG. 10.

The wavelet-transform coefficient signal HL1 represents a low frequency component in the vertical scanning direction and, as shown in FIG. 10, contains both a vertical grid component and an image signal which has the vertical direction of an original image signal as its main component. If the signal HL1 is subjected to one-dimensional wavelet transformation in a grid length direction (in this embodiment, vertical scanning direction), the grid component in the case of a vertical grid is considered to be a one-dimensional frequency signal which is vertically long, and therefore, band split is made so that a low frequency component containing the vertical grid component is contained in the signal HL1 (Lj) and the other high frequency components are contained in the signal HL1 (Hj). If this one-dimensional wavelet transformation is repeatedly given, a low frequency signal HL1 (Lm) in which band split has sufficiently been made represents an extremely low frequency component which contains a grid component in the grid length direction independently of grid pitch size. If the "m" in the signal HL1 (Lm) becomes greater, the signal will represent only a grid component.

Actually, in most cases, the stationary grid is not perfectly placed horizontally, vertically, or in a crossing direction where "horizontal" and "vertical" are 1:1. Therefore, too great a number (m) of repeats will cause the grid component to develop in the signal HL1 (Hj). Thus, it is preferable that one-dimensional wavelet transformation be repeated a few times.

Next, among the signals HL1 (H1) to HL1 (Hm), and HL1 (Lm) obtained by applying one-dimensional wavelet transformation to the signal HL1 in the vertical scanning direction over a plurality of stages, the signal HL1 (Lm) which is a component on the lowest frequency side is made zero. That is, the signal HL1 (Lm) containing a grid component is suppressed. Thereafter, the signal HL1 (Lm), made zero, and the signals HL1 (HL) to HL1 (Hm), are subjected to inverse one-dimensional wavelet transformation, whereby a signal HL1' is obtained. As previously described, at least the signal HL1 (Lm) containing the spatial frequency component of the stationary grid 4 has been suppressed. Therefore, the signal HL1', in which the spatial frequency component with a predetermined frequency range containing the grid component has been reduced, is obtained.

Next, in the processing means 33 a desired process (e.g., an enhancing process) is applied as occasion demands. Thereafter, in the inverse wavelet transform section 34, the signals LLn, HLk, and LHk are sequentially subjected to inverse wavelet transformation from level n to level 1.

Figure 11:
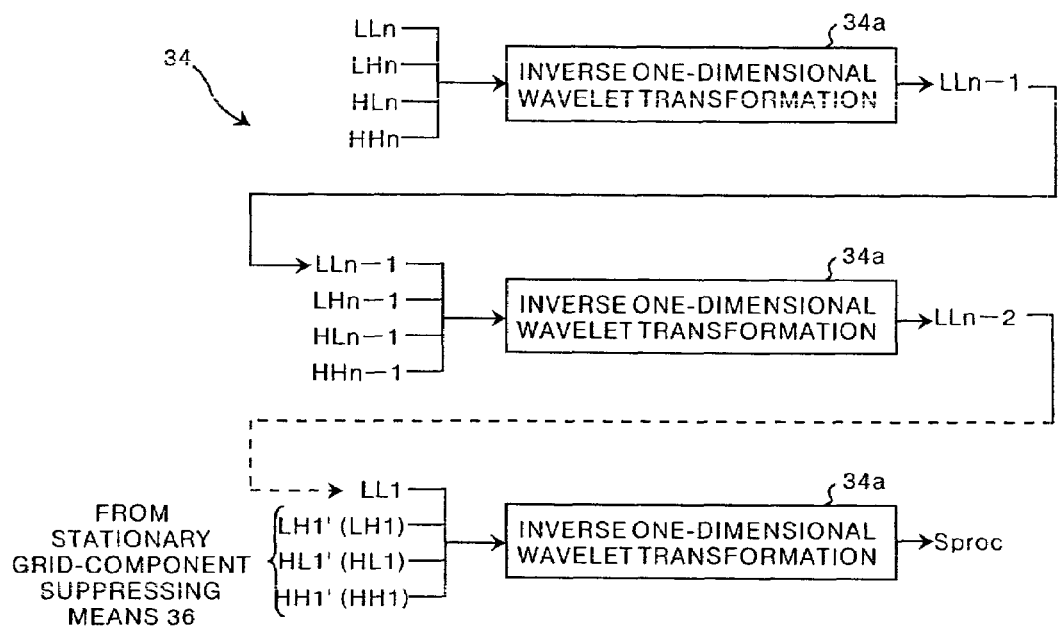
FIG. 11 is a block diagram showing the construction of an inverse wavelet transform section.

FIG. 11 shows the construction of the inverse wavelet transform section 34. As shown in the figure, in the inverse wavelet transform means 34a the lowest frequency band signals HHn, HLn, LHn, and LLn are subjected to inverse wavelet transformation, whereby an signal LLn-1 is obtained.

Figure 12:
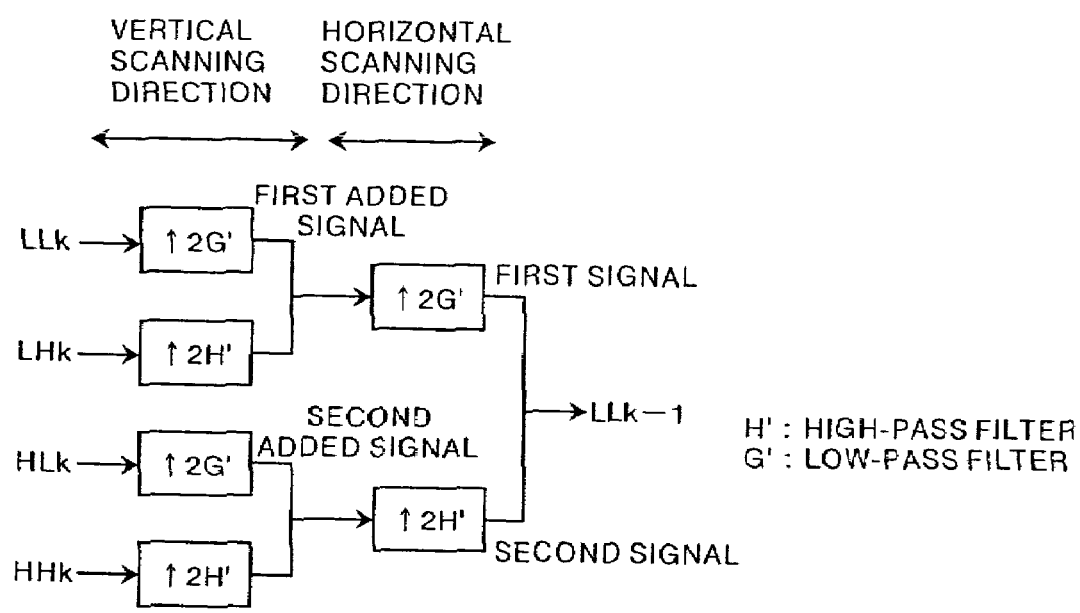
FIG. 12 is a block diagram showing how inverse wavelet transformation is performed by the wavelet transform section shown in FIG. 11.

FIG. 12 shows how the inverse wavelet transformation is performed by each wavelet transform means 34a. As shown in the figure, signals LLn (LLk) and LHn (LHk) are subjected to a process for leaving space for 1 pixel between adjacent pixels, in the vertical direction. This process is represented by "↑2" in FIG. 12. The signals are also subjected to a filtering process in the vertical scanning direction by the inverse wavelet transform functions G0', H0' corresponding to the functions G0', H0' employed in performing wavelet transformation, and are added. Furthermore, the signal obtained by addition (referred to as a first added signal) is subjected to the aforementioned space leaving process in the horizontal scanning direction, and is subjected to the filtering process in the horizontal direction by the function G0'. In this manner, a first signal is obtained. On the other hand, signals HLn (HLk) and HHn (HHk) are subjected to the process for leaving space for 1 pixel between adjacent pixels, in the vertical direction. The signals are also subjected to the filtering process in the vertical scanning direction by the inverse wavelet transform functions G0', H0', and are added. Furthermore, the signal obtained by addition (referred to as a second added signal) is subjected to the process for leaving space for 1 pixel between adjacent pixels, in the horizontal scanning direction, and is also subjected to the filtering process in the horizontal direction by the function H0'. In this way, a second signal is obtained. The first signal and the second signal are added, whereby a signal LLn-1 (LLk-1) is obtained.

Next, in the inverse wavelet transform means 34a, signals HHn-1, HLn-1, and LLn-1 are subjected to inverse wavelet transformation in the same manner as the aforementioned, whereby a processed signal LLn-2 is obtained. In the same way as the aforementioned, a signal LL1 is obtained by repeating inverse wavelet transformation down to resolution level 1.

At the resolution level 0 representing the original image, the signals LL1, LH1, HH1, and HL1' are subjected to inverse wavelet transformation by the inverse wavelet transform functions G1', H1' corresponding to the functions G1, H1 employed in performing wavelet transformation at the initial stage, whereby an image is reconstructed. Note that the signal HL1' has been reduced in grid component. In the reconstructed image, therefore, the grid component of the stationary grid 4 has been reduced.

FIG. 13 is used to explain advantages of the present invention. FIG. 13A illustrates a frequency response characteristic obtained in the case of a method described in Japanese Unexamined Patent Publication No. 10(1998)-164737 (hereinafter referred to as a conventional method). FIG. 13B illustrates a frequency response characteristic obtained in the case of the present invention, and FIG. 13C illustrates the frequency response characteristics in Fourier space obtained by the conventional method and the method according to the present invention. Note that FIG. 13C illustrates the case where a vertical stationary grid is employed in the Fourier space with the horizontal scanning direction as a v-axis and the vertical scanning direction as a u-axis.

In the case of the conventional method, a filter is employed in which not only its response at a frequency near a spatial frequency corresponding to the grid pitch of a stationary grid, but also its response at a high frequency component greater than that, is made zero. Therefore, as shown in FIG. 13A, the high frequency component greater than the spatial frequency corresponding to the grid pitch is also suppressed. As a result, not only the stripe pattern of the stationary grid 4, but also the high frequency component originally contained in the image, is removed and reduced. Because of this, the image will be reduced in sharpness. In addition, because the filtering process in the conventional method is not a filtering process taking direction into consideration, all (oblique line portion) other than a low frequency domain (central blank portion) on the Fourier space is suppressed as shown FIG. 13C. That is, not only a vertical pattern due to a vertical grid (which is desired to be really suppressed) but also a high frequency component, which is not desired to be suppressed, such as a horizontal pattern, a diagonal pattern, etc., which are contained in the original image, is suppressed.

On the other hand, in the case of the present invention, even if a filter exhibiting the same characteristic as that described in the aforementioned Japanese Unexamined Patent Publication No. 10(1998)-164737 is used as the filter employed in the wavelet transformation at the initial stage, only a predetermined range near the spatial frequency component of the stationary grid 4 can be suppressed (or cut) and the remaining high frequency components sustained, as shown in FIG. 13B. Therefore, an image, in which a stripe pattern due to the stationary grid is inconspicuous and sharpness is high, can be obtained. In addition, the signals HL1, LH1, and HH1 can be switched according to the grid direction so that only a signal of the signals HL1, LH1, and HH1 which contains the grid component is suppressed. Therefore, as shown in FIG. 13C, only a predetermined range on the high frequency side can be suppressed. The predetermined range on the high frequency side is in a domain (with a slight width in a direction perpendicular to grid direction) near the grid-direction axis (in the case of a vertical grid, v-axis) of the Fourier space, and contains the spatial frequency component of the stationary grid 4. For example, in the case of a vertical grid, only a vertical pattern due to the grid is suppressed and there is no possibility that a high frequency component, such as a horizontal pattern, a diagonal pattern, etc., which is contained in the original image, will be suppressed.

In addition, the direction of a grid can be judged, based on the wavelet-transform coefficient signals HH1, HL1, and LH1 having a possibility of containing the grid component, among the wavelet-transform coefficient signals HH1, HL1, LH1, and LL1 obtained by two-dimensional wavelet transformation at the initial stage. Therefore, when performing the process of suppressing a grid component, there is no necessity for previously knowing what kind of grid is used in photographing.

Furthermore, if signals are restored to resolution level 1 without being restored to resolution level 0, a stripe pattern resulting from the stationary grid 4 will barely develop, because, as previously described, in the signal LL1 the spatial frequency component of the stationary grid 4 is sufficiently suppressed. Moreover, since the signal LLk after level 1, obtained by giving wavelet transformation to the signal LL1 in which the grid component has been suppressed, does not contain a moire component, there is no possibility that in all reduced-scale images, a moire pattern resulting from the stationary grid 4 will occur. Even if the image is arbitrarily enlarged or reduced, no moire pattern will occur. Therefore, even if an image is subjected to a desired process such as an enhancing process and the processed image is restored by inverse multiresolution transformation, the restored image will contain no artifact due to the moire pattern even if it has any resolution level. As a result, a high-quality image which is easy to view can be provided.

Thus, since the grid component is suppressed by wavelet transformation (multiresolution transformation) at the initial stage, a moire pattern will no longer develop in the images having the subsequent resolution levels. In addition, because wavelet transformation is employed, this embodiment is suitable for obtaining an enlarged- or reduced-scale image and is also convenient in transferring image signals through networks.

While the present invention has been described with reference to a preferred embodiment thereof, the invention is not to be limited to the details given herein, but may be modified within the scope of the invention hereinafter claimed.

For example, while it has been described that the stationary grid 4 is a vertical grid, if it is other than the vertical grid the signal HL1 to be handled may be the signal LH1 or HH1, depending on the grid direction. For example, in the case where the stationary grid 4 is a horizontal grid, the signal LH1 is further subjected to one-dimensional wavelet transformation in the horizontal scanning direction over a plurality of stages. After the signal component on the low frequency side is made zero, inverse one-dimensional wavelet transformation is applied to reconstruct the image. In the case where the stationary grid 4 is a cross grid, the signals HL and LH are further subjected to one-dimensional wavelet transformation in the vertical and horizontal scanning directions over a plurality of stages, respectively. After the signal component on the low frequency side is made zero, inverse one-dimensional wavelet transformation is applied to reconstruct the image.

Instead of applying one-dimensional wavelet transformation to the signal HL and/or signal LH, a high-pass filter for reducing a grid component may be employed.

If a stationary grid to be used is subjected to the aforementioned processing in each grid direction independently of the direction of a grid which is actually used, for example, and if in addition to the processing shown in FIG. 9, the signal LH1 is repeatedly subjected to one-dimensional wavelet transformation in the horizontal scanning direction, the suppressing effect can be obtained not only in a predetermined range on the high frequency side near the v-axis shown in FIG. 13C, which contains the spatial frequency component of the stationary grid 4, but also in a predetermined range on the high frequency side near the u-axis, which contains the spatial frequency component of the stationary grid 4. In many cases, a grid of the same direction as either of horizontal and vertical scanning directions is usually employed. In those cases, the grid component will be contained in either the signal HL (when a vertical grid is used) or signal LH1 (when a horizontal grid is used), and consequently, the effect of the aforementioned suppressing process can be obtained without considering grid direction. Also, in those cases, since the suppressing process is not applied in infinite directions but is limited only to each grid direction in which the suppressing process is to be performed, the influence of the suppressing process on an image can be reduced, compared with prior art. Note that a cross grid can be handled by repeatedly applying one-dimensional wavelet transformation to the signal HHL in both the horizontal and vertical scanning directions.

Figure 14:
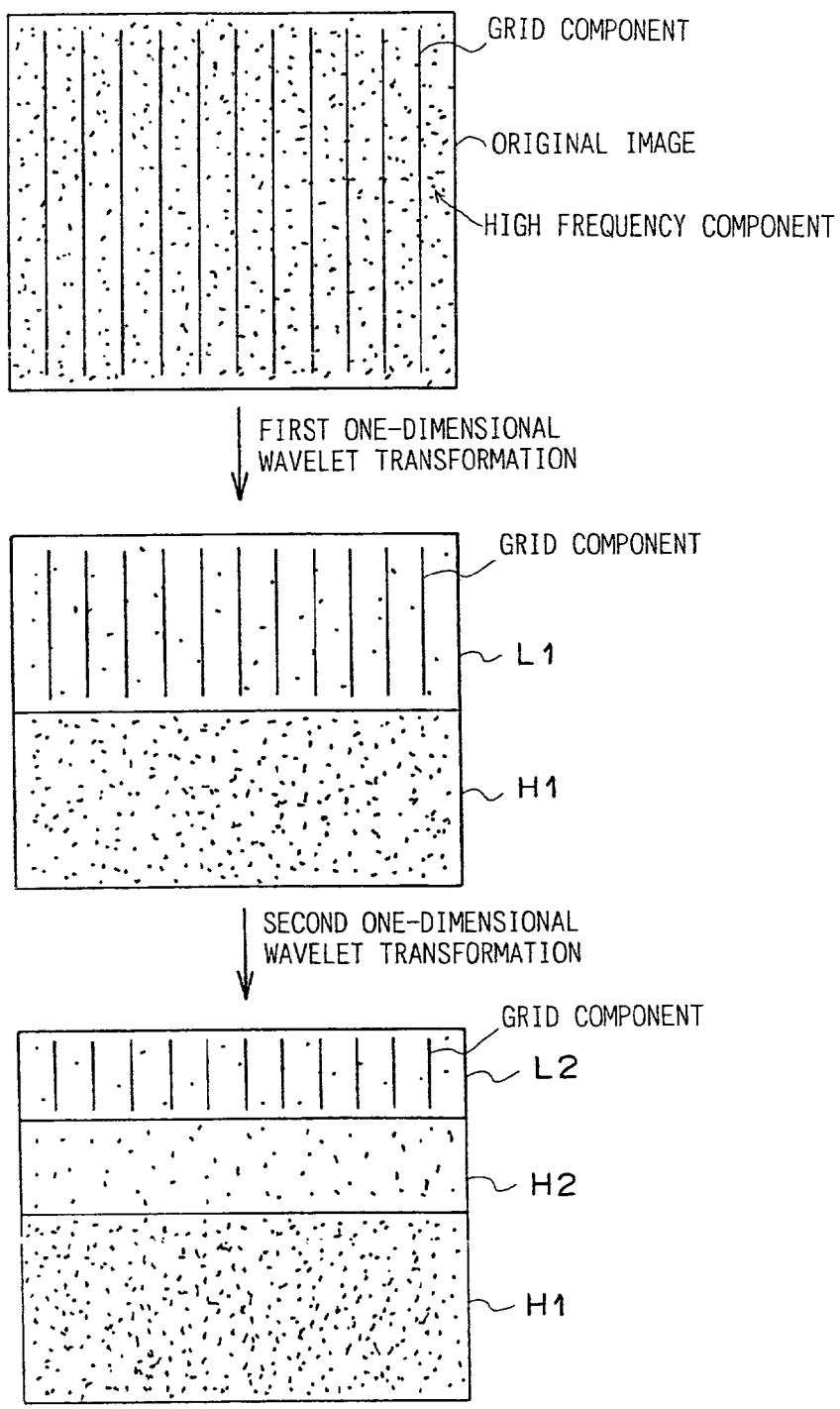
FIG. 14 is a diagram showing another embodiment of the present invention.

In this embodiment, it has been described that the image signal S is subjected to two-dimensional wavelet transformation. However, in the case where grid direction is known, the original image signal may be subjected to one-dimensional wavelet transformation in that direction (in the vertical scanning direction when the grid is a vertical grid), and the wavelet-transform coefficient signal containing a grid component (signal L1 of FIG. 14B) subjected to the process of reducing a grid component, as shown in FIG. 14. Note that the wavelet function which is employed in performing one-dimensional wavelet transformation may be an arbitrary one. For instance, the aforementioned functions H0, G0 can be employed.

If the method shown in FIG. 14 is employed, an extremely low frequency component representing grid-length direction will develop in a low frequency wavelet-transform coefficient signal (signal L1) of the wavelet-transform coefficient signals. After the wavelet-transform coefficient signal L1 has repeatedly been subjected to the process of reducing a grid component (e.g., one-dimensional wavelet transformation in the same direction) (see FIG. 14C), the lowest frequency wavelet-transform coefficient signal is made zero, or only signal components representing the original image other than the grid component are extracted with a high-pass filter. In this way, an extremely low frequency component representing the grid component can be suppressed.

Thus, when an image is restored by applying one-dimensional wavelet transformation to the signal in which the grid component has been reduced, an image with a reduced grid component can be restored regardless of the resolution level at which the image is restored.

In the embodiment shown in FIG. 14, the above-mentioned processing can also be applied in each grid direction of a stationary grid to be used, independently of the grid direction that is actually used. For example, in addition to the processing in the vertical scanning direction shown in FIG. 14, the processing is performed in the horizontal scanning direction. Between two images finally obtained, the image with fewer grid components can be used.

It has been described that when the image signal S represented in a real space domain is transformed into a plurality of image signal which can be handled in a frequency domain, the multiresolution decomposing process employing the wavelet transform process is used. However, any method of transformation can be employed as long as it can apply a process of reducing a component which has a desired frequency range containing a stationary grid component contained in an image signal. For example, a multiresolution decomposing process employing a Laplacian pyramid expansion can also be employed. Also, an image signal expressed in the real space domain may be transformed by Fourier transformation into image signals expressed in a frequency domain (frequency spectra).

In addition, all of the contents of Japanese Patent Application Nos.2000-011174 and 2000-395577 are incorporated into this specification by reference.

What is claimed is:

1. A periodic-pattern suppression method of reducing a spatial frequency component resulting from a stationary grid, contained in an original image signal photographed using said stationary grid, said method comprising the steps of:

transforming said original image signal, represented in a real space domain, into a plurality of transformed image signals which can be handled in a frequency domain; and reducing a transformed image signal of said transformed image signals which has a desired frequency range containing a spatial frequency component corresponding to at least a grid array frequency of said stationary grid, which is actually used, in only the vicinity of a grid array direction of said stationary grid, not reducing any of said transformed image signals in a different direction from said vicinity of said array direction of said periodic pattern, and then transforming said transformed image signals into an inverse-transformed signal in said real space domain, wherein said transforming step obtains said plurality of transformed image signals by applying two-dimensional wavelet transformation to said original image signal by the use of a low-pass filter which splits a band so that its response at a frequency greater than the spatial frequency of said stationary grid becomes approximately zero; and said reducing step further applies a process of reducing a component less than a predetermined frequency and then performs inverse wavelet transformation, with respect to a signal of said transformed image signals which contains a spatial frequency component corresponding to said grid array frequency.

2. The periodic-pattern suppression method as set forth in claim 1, wherein said reducing step reduces a component less than said predetermined frequency, by recursively and repeatedly applying one-dimensional wavelet transformation to the transformed image signal, containing a spatial frequency component corresponding to said grid array frequency, in a grid array direction of said stationary grid by a predetermined number of times by the use of a predetermined band splitting filter, then making zero transform coefficients of a low frequency image signal of a plurality of image signals obtained by said one-dimensional wavelet transformation, and applying inverse one-dimensional wavelet transformation.

3. The periodic-pattern suppression method as set forth in claim 2, wherein said reducing step calculates powers of said plurality of transformed image signals, judges the grid length direction of said stationary grid, based on whether or not each said calculated power is greater than a predetermined threshold value, and applies said process of reducing a component less than a predetermined frequency, based on the result of judgment.

4. The periodic-pattern suppression method as set forth in claim 2, wherein said reducing step reduces a component less than said predetermined frequency, by recursively and repeatedly applying one-dimensional wavelet transformation to the transformed image signal, containing a spatial frequency component corresponding to said grid array frequency, in a grid array direction of each possible stationary grid that may be used by a predetermined band splitting filter, then making zero transform coefficients of a low frequency image signal of a plurality of image signals obtained by said one-dimensional wavelet transformation, and applying inverse one-dimensional wavelet transformation.

5. The periodic-pattern suppression method as set forth in claim 1, wherein said reducing step calculates powers of said plurality of transformed image signals, judges the grid length direction of said stationary grid, based on whether or not each said calculated power is greater than a predetermined threshold value, and applies said process of reducing a component less than a predetermined frequency, based on the result of judgment.

6. The periodic-pattern suppression method as set forth in claim 1, wherein said reducing step reduces a component less than said predetermined frequency with respect to a signal of said transformed image signals wherein said reduction comprises reducing a spatial frequency component corresponding to a grid array frequency of each possible stationary grid that may be used and then performs inverse wavelet transformation.

7. A periodic-pattern suppression method of reducing a spatial frequency component resulting from a stationary grid, contained in an original image signal photographed using said stationary grid, said method comprising the steps of:
transforming said original image signal, represented in a real space domain, into a plurality of transformed image signals which can be handled in a frequency domain; and
reducing a transformed image signal of said transformed image signals which has a desired frequency range containing a spatial frequency component corresponding to at least a grid array frequency of said stationary grid, which is actually used, in only the vicinity of a grid array direction of said stationary grid, not reducing any of said transformed image signals in a different direction from said vicinity of said array direction of said periodic pattern, and then transforming said transformed image signals into an inverse-transformed signal in said real space domain, wherein
said transforming step obtains said plurality of transformed image signals by applying one-dimensional wavelet transformation to said original image signal in the grid length direction of said stationary grid by the use of a predetermined band splitting filter; and
said reducing step further applies a process of reducing a component less than a predetermined frequency and then performs inverse wavelet transformation, with respect to a low frequency image signal of said transformed image signals which contains a spatial frequency component corresponding to the grid array frequency of said stationary grid.

8. The periodic-pattern suppression method as set forth in claim 7, wherein each stationary grid to be used is subjected to said transforming step and said reducing step.

9. A periodic-pattern suppression unit for reducing a spatial frequency component resulting from a stationary grid, contained in an original image signal photographed using said stationary grid, said unit comprising:
image signal transforming means for transforming said original image signal, represented in a real space domain, into a plurality of transformed image signals which can be handled in a frequency domain; and
stationary grid-component suppressing means for reducing a transformed image signal of said transformed image signals which has a desired frequency range containing a spatial frequency component corresponding to at least a grid array frequency of said stationary grid, which is actually used, in only the vicinity of a grid array direction of said stationary grid, not reducing any of said transformed image signals in a different direction from said vicinity of said array direction of said periodic pattern, and then transforming said transformed image signals into an inverse-transformed signal in said real space domain, wherein
said image signal transforming means obtains said plurality of transformed image signals by applying two-dimensional wavelet transformation to said original image signal by the use of a low-pass filter which splits a band so that its response at a frequency greater than the spatial frequency of said stationary grid becomes approximately zero; and
said stationary grid-component suppressing means further applies a process of reducing a component less than a predetermined frequency and then performs inverse wavelet transformation, with respect to an image signal of said transformed image signals which contains a spatial frequency component corresponding to the grid array frequency of said stationary grid.

10. The periodic-pattern suppression unit as set forth in claim 9, wherein said stationary grid-component suppressing means reduces a component less than said predetermined frequency, by recursively and repeatedly applying one-dimensional wavelet transformation to the transformed image signal, containing a spatial frequency component corresponding to said grid array frequency, in a grid array direction of said stationary grid by a predetermined number of times by the use of a predetermined band splitting filter, then making zero transform coefficients of a low frequency image signal of a plurality of image signals obtained by said one-dimensional wavelet transformation, and applying inverse one-dimensional wavelet transformation.

11. The periodic-pattern suppression unit as set forth in claim 10, further comprising stationary grid-direction judging means for calculating powers of said plurality of transformed image signals and judging the grid length direction of said stationary grid, based on whether or not each said calculated power is greater than a predetermined threshold value;
wherein said stationary grid-direction judging means applies said process of reducing a component less than a predetermined frequency, based on the judgment made by said stationary grid-direction judging means.

12. The periodic-pattern suppression unit as set forth in claim 10, wherein said stationary grid-component suppressing means applies said process of reducing a component less than a predetermined frequency, by recursively and repeatedly applying one-dimensional wavelet transformation to the transformed image signal, containing a spatial frequency component corresponding to said grid array frequency, in a grid array direction of each possible stationary grid that may be used by a predetermined number of times by the use of a predetermined band splitting filter, then making zero transform coefficients of a low frequency image signal of a plurality of image signals obtained by said one-dimensional wavelet transformation, and applying inverse one-dimensional wavelet transformation.

13. The periodic-pattern suppression unit as set forth in claim 9, further comprising stationary grid-direction judging means for calculating powers of said plurality of transformed image signals and judging the grid length direction of said stationary grid, based on whether or not each said calculated power is greater than a predetermined threshold value;
wherein said stationary grid-component suppressing means applies said process of reducing a component less than a predetermined frequency, based on the judgment made by said stationary grid-direction judging means.

14. The periodic-pattern suppression unit as set forth in claim 9, wherein said stationary grid-component suppressing means applies said process of reducing a component less than a predetermined frequency with respect to an image signal of said transformed image signals wherein said reduction comprises reducing a spatial frequency component corresponding to the grid array frequency of each possible stationary grid that may be used and then performs inverse wavelet transformation.

15. A periodic-pattern suppression unit for reducing a spatial frequency component resulting from a stationary grid, contained in an original image signal photographed using said stationary grid, said unit comprising:
image signal transforming means for transforming said original image signal, represented in a real space domain, into a plurality of transformed image signals which can be handled in a frequency domain; and
stationary grid-component suppressing means for reducing a transformed image signal of said transformed image signals which has a desired frequency range containing a spatial frequency component corresponding to at least a grid array frequency of said stationary grid, which is actually used, in only the vicinity of a grid array direction of said stationary grid, not reducing any of said transformed image signals in a different direction from said vicinity of said array direction of said periodic pattern, and then transforming said transformed image signals into an inverse-transformed signal in said real space domain, wherein
said image signal transforming means obtains said plurality of transformed image signals by applying one-dimensional wavelet transformation to said original image signal in the grid length direction of said stationary grid by the use of a predetermined band splitting filter; and
said stationary grid-component suppressing means further applies a process of reducing a component less than a predetermined frequency and then performs inverse wavelet transformation, with respect to a low frequency image signal of said transformed image signals which contains a spatial frequency component corresponding to the grid array frequency of said stationary grid.

16. The periodic-pattern suppression unit as set forth in claim 15, wherein
said image signal transforming means applies said one-dimensional wavelet transformation in the grid length direction of each stationary grid to be used; and
said stationary grid-component suppressing means applies said reducing process and said inverse wavelet transformation to each said stationary grid to be used.

17. A periodic-pattern suppression method of reducing a spatial frequency component resulting from a stationary grid, contained in an original image signal photographed using said stationary grid, said method comprising the steps of:
transforming said original image signal, represented in a real space domain, into a plurality of transformed image signals which can be handled in a frequency domain; and
reducing a transformed image signal of said transformed image signals which has a desired frequency range containing a spatial frequency component corresponding to at least a grid array frequency of said stationary grid, which is actually used, in only the vicinity of a grid array direction of said stationary grid, not reducing any of said transformed image signals in a different direction from said vicinity of said array direction of said periodic pattern, and then transforming said transformed image signals into an inverse-transformed signal in said real space domain, wherein said reducing step reduces a component less than a predetermined frequency, by recursively and repeatedly applying one-dimensional wavelet transformation to the transformed image signal, containing a spatial frequency component corresponding to said grid array frequency, in a grid array direction of said stationary grid by a predetermined number of times by the use of a predetermined band splitting filter, then making zero transform coefficients of a low frequency image signal of a plurality of image signals obtained by said one-dimensional wavelet transformation, and applying inverse one-dimensional wavelet transformation.

18. A periodic-pattern suppression unit for reducing a spatial frequency component resulting from a stationary grid, contained in an original image signal photographed using said stationary grid, said unit comprising:
image signal transforming means for transforming said original image signal, represented in a real space domain, into a plurality of transformed image signals which can be handled in a frequency domain; and
stationary grid-component suppressing means for reducing a transformed image signal of said transformed image signals which has a desired frequency range containing a spatial frequency component corresponding to at least a grid array frequency of said stationary grid, which is actually used, in only the vicinity of a grid array direction of said stationary grid, not reducing any of said transformed image signals in a different direction from said vicinity of said array direction of said periodic pattern, and then transforming said transformed image signals into an inverse-transformed signal in said real space domain, wherein said stationary grid-component suppressing means reduces a component less than a predetermined frequency, by recursively and repeatedly applying one-dimensional wavelet transformation to the transformed image signal, containing a spatial frequency component corresponding to said grid array frequency, in a grid array direction of said stationary grid by a predetermined number of times by the use of a predetermined band splitting filter, then making zero transform coefficients of a low frequency image signal of a plurality of image signals obtained by said one-dimensional wavelet transformation, and applying inverse one-dimensional wavelet transformation.

19. A periodic-pattern suppression method of reducing a spatial frequency component which forms a periodic pattern contained in an original image signal, said method comprising the steps of:
transforming said original image signal, represented in a real space domain, into a plurality of transformed image signals which can be handled in a frequency domain; and
reducing a transformed image signal of said transformed image signals which has a desired frequency range containing a spatial frequency component corresponding to at least a frequency of said periodic pattern in only the vicinity of an array direction of said periodic pattern, not reducing any of said transformed image signals in a different direction from said vicinity of said array direction of said periodic pattern, and then transforming said transformed image signals into an inverse-transformed signal in said real space domain, wherein said reducing a transformed image signal comprises reducing the transformed image signal by extracting a low frequency component in a direction perpendicular to said array direction from said transformed image signal containing at least said spatial frequency component corresponding to said frequency of said periodic pattern in said array direction, said low frequency component having a spatial frequency lower than a predetermined value, and then reducing said extracted low frequency component.

20. A periodic-pattern suppression unit for reducing a spatial frequency component which forms a periodic pattern contained in an original image signal, said unit comprising the steps of:
   image signal transformation means for transforming said original image signal, represented in a real space domain, into a plurality of transformed image signals which can be handled in a frequency domain; and
   periodic-pattern-component suppression means for reducing a transformed image signal of said transformed image signals which has a desired frequency range containing a spatial frequency component corresponding to at least a frequency of said periodic pattern in only the vicinity of an array direction of said periodic pattern, not reducing any of said transformed image signals in a different direction from said vicinity of said array direction of said periodic pattern, and then transforming said transformed image signals into an inverse-transformed signal in said real space domain, wherein said periodic-pattern-component suppression means reduces the transformed image signal by extracting a low frequency component in a direction perpendicular to said array direction from said transformed image signal containing at least said spatial frequency component corresponding to said frequency of said periodic pattern in said array direction, said low frequency component having a spatial frequency lower than a predetermined value, and then reducing said extracted low frequency component.

* * * * *